US012643875B2

(12) United States Patent
Keiler et al.

(10) Patent No.: US 12,643,875 B2
(45) Date of Patent: Jun. 2, 2026

(54) ANTIBACTERIAL COMPOUNDS

(71) Applicant: The Penn State Research Foundation, University Park, PA (US)

(72) Inventors: Kenneth C. Keiler, University Park, PA (US); John N. Alumasa, University Park, PA (US); Sarah Ellen Ades, University Park, PA (US)

(73) Assignee: The Penn State Research Foundation, University Park, PA (US)

(*) Notice: Subject to any disclaimer, the term of this patent is extended or adjusted under 35 U.S.C. 154(b) by 770 days.

(21) Appl. No.: 17/926,437

(22) PCT Filed: May 27, 2021

(86) PCT No.: PCT/US2021/034509

§ 371 (c)(1),
(2) Date: Nov. 18, 2022

(87) PCT Pub. No.: WO2021/243015

PCT Pub. Date: Dec. 2, 2021

(65) Prior Publication Data

US 2023/0183203 A1 Jun. 15, 2023

Related U.S. Application Data

(60) Provisional application No. 63/030,673, filed on May 27, 2020.

(51) Int. Cl.

| | |
|---|---|
| ***C07D 401/14*** | (2006.01) |
| ***A01N 37/22*** | (2006.01) |
| ***A01N 43/40*** | (2006.01) |
| ***A01N 43/647*** | (2006.01) |
| ***A01N 43/82*** | (2006.01) |
| ***A01P 1/00*** | (2006.01) |
| ***A61K 45/06*** | (2006.01) |
| ***A61P 31/04*** | (2006.01) |
| ***C07C 233/65*** | (2006.01) |
| ***C07C 233/66*** | (2006.01) |
| ***C07C 317/36*** | (2006.01) |
| ***C07D 213/74*** | (2006.01) |
| ***C07D 213/75*** | (2006.01) |
| ***C07D 213/76*** | (2006.01) |
| ***C07D 307/68*** | (2006.01) |
| ***C07D 401/04*** | (2006.01) |
| ***C07D 405/12*** | (2006.01) |
| ***C07D 409/04*** | (2006.01) |
| ***C07D 413/12*** | (2006.01) |
| ***C07F 7/08*** | (2006.01) |

(52) U.S. Cl.

CPC ........... *C07D 401/04* (2013.01); *A01N 37/22* (2013.01); *A01N 43/40* (2013.01); *A01N 43/647* (2013.01); *A01N 43/82* (2013.01); *A01P 1/00* (2021.08); *A61K 45/06* (2013.01); *A61P 31/04* (2018.01); *C07C 233/65* (2013.01); *C07C 233/66* (2013.01); *C07C 317/36* (2013.01); *C07D 213/74* (2013.01); *C07D 213/75* (2013.01); *C07D 213/76* (2013.01); *C07D 307/68* (2013.01); *C07D 405/12* (2013.01); *C07D 409/04* (2013.01); *C07D 413/12* (2013.01); *C07F 7/0812* (2013.01)

(58) Field of Classification Search

CPC .. C07D 401/04; C07D 213/74; C07D 213/75; C07D 213/76; C07D 307/68; C07D 405/12; C07D 409/04; C07D 413/12; C07D 417/04; A01N 37/22; A01N 43/40; A01N 43/647; A01N 43/82; A01P 1/00; A61K 45/06; A61P 31/04; A61P 31/02; C07C 233/65; C07C 233/66; C07C 317/36; C07F 7/0812

See application file for complete search history.

(56) References Cited

U.S. PATENT DOCUMENTS

| | | | | |
|---|---|---|---|---|
| 4,118,487 | A * | 10/1978 | Regel .................. | C07D 249/08 568/30 |
| 5,304,121 | A | 4/1994 | Sahatjian | |
| 5,886,026 | A | 3/1999 | Hunter et al. | |
| 6,099,562 | A | 8/2000 | Ding et al. | |
| 6,803,031 | B2 | 10/2004 | Rabinowitz et al. | |
| 7,014,866 | B2 | 3/2006 | Infeld et al. | |
| 8,962,550 | B2 | 2/2015 | Ades et al. | |
| 2006/0074237 | A1 | 4/2006 | Amrein et al. | |
| 2006/0079502 | A1 | 4/2006 | Lang | |
| 2006/0094744 | A1 | 5/2006 | Maryanoff et al. | |
| 2014/0329840 | A1* | 11/2014 | Srinivasan ........... | C07D 487/04 435/375 |

(Continued)

FOREIGN PATENT DOCUMENTS

| | | | | |
|---|---|---|---|---|
| EP | 1016659 A1 * | 7/2000 | .......... C08F 290/145 | |
| EP | 1574504 | 9/2005 | | |

(Continued)

OTHER PUBLICATIONS

Emmerich, et al.; Journal of Medicinal Chemistry, v56, pp. 6022-6032; 2013 (Year: 2013).*

(Continued)

*Primary Examiner* — Jeffrey S Lundgren

*Assistant Examiner* — W. Justin Youngblood

(74) *Attorney, Agent, or Firm* — Fish & Richardson P.C.

(57) ABSTRACT

The present application provides antibiotic compounds, as well as pharmaceutical compositions comprising these compounds, and methods of treating bacterial infections using these compounds.

20 Claims, No Drawings

(56) References Cited

U.S. PATENT DOCUMENTS

2019/0189927 A1 6/2019 Lee et al.

FOREIGN PATENT DOCUMENTS

| | | | | |
|---|---|---|---|---|
| EP | 1683804 | | 7/2006 | |
| EP | 3385254 | | 10/2018 | |
| WO | WO 2003/033457 | | 4/2003 | |
| WO | WO 2003/051092 | | 6/2003 | |
| WO | WO-2006010637 | A2 * | 2/2006 | ........... C07D 213/74 |
| WO | WO 2006/067466 | | 6/2006 | |
| WO | WO 2006/076009 | | 7/2006 | |
| WO | WO-2009021696 | A1 * | 2/2009 | .............. A61P 37/00 |
| WO | WO 2012041476 | | 4/2012 | |
| WO | WO-2012041476 | A1 * | 4/2012 | .............. A61P 43/00 |
| WO | WO 2015/103355 | A1 | 7/2015 | |
| WO | WO 2016/131739 | A1 | 8/2016 | |
| WO | WO 2019/040404 | | 2/2019 | |

OTHER PUBLICATIONS

International Preliminary Report on Patentability in International Appln. No. PCT/US2021/034509, mailed on Dec. 8, 2022, 7 pages.

International Search Report and Written Opinion in International Appln. No. PCT/US2021/034509, mailed on Oct. 12, 2021, 10 pages.

PubChem, "SID 376212696," Nov. 8, 2018, retrieved on Feb. 14, 2023, retrieved from URL < https://pubchem.ncbi.nlm.nih.gov/substance/376212696>, 4 pages.

Chen et al., "Sequential C—S and S—N Coupling Approach to Sulfonamides," Org. Lett., Mar. 2020, 22(5):1841-1845.

Cirulli et al., "Rotaxane-Based Transition Metal Complexes: Effect of the Mechanical Bond on Structure and Electronic Properties," J. Am. Chem. Soc., Jan. 2019, 141(2):879-889.

Extended European Search Report in European Appln. No. 21814416.0, dated Oct. 24, 2023, 11 pages.

Heitman et al., "False positives in a reporter gene assay: identification and synthesis of substituted N-pyridin-2-ylbenzamides as competitive inhibitors of firefly luciferase," J. Med. Chem., Aug. 2008, 51(15):4724-4729.

Keiler, "Inhibitors of the σE virulence pathway as novel antibiotics," Presented at Biotech Discovery Day, Penn State University, Jun. 12, 2020, 1 page.

CAS No. 2257492-28-5, "2-(3,5-ditert-butylphenyl)-6-[1-(3,5-ditert-butylphenyl)triazol-4-yl]pyridine," Chemical.Patsnap.com, Dec. 18, 2018, retrieved on Aug. 18, 2025, retrieved from URL<https://chemical.patsnap.com/search#/detail/1516530882c347d4ada700e7420679f7/overview>, 1 page.

* cited by examiner

ANTIBACTERIAL COMPOUNDS

CROSS-REFERENCE TO RELATED APPLICATIONS

This application is a National Stage application under 35 U.S.C. § 371 of International Application No. PCT/US2021/034509, having an International Filing Date of May 27, 2021, which claims priority to U.S. Provisional Patent Application Ser. No. 63/030,673, filed on May 27, 2020, the entire contents of which are hereby incorporated by reference.

STATEMENT AS TO FEDERALLY SPONSORED RESEARCH

This invention was made with government support under Grant No. GM097365 awarded by the National Institutes of Health. The Government has certain rights in the invention.

TECHNICAL FIELD

This invention relates to antibiotic compounds, and in some embodiments to biphenyl compounds that are inhibitors of bacterial virulence.

BACKGROUND

Bacterial infections remain one of the leading causes of death worldwide. Particularly, the persistence of bacterial strains that are resistant to antibiotics poses a threat to human health. Absolute numbers of infections due to resistant microbes are increasing globally.

SUMMARY

A conserved transcription factor, σE, is essential for viability or virulence in many bacterial pathogens, including Gram-negative bacterial pathogens. Compounds described herein advantageously inhibit σE, and, therefore, are useful as a bactericidal or bacteriostatic antibacterial agents.

In one general aspect, the present disclosure provides a compound of Formula (I):

(I)

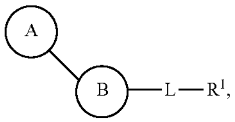

or a pharmaceutically acceptable salt thereof, wherein ring A, ring B, L, and $R^1$ are as described herein.

In another general aspect, the present disclosure provides a pharmaceutical composition comprising the compound of Formula (I), pharmaceutically acceptable salt thereof, and a pharmaceutically acceptable carrier.

In yet another general aspect, the present disclosure provides a cleaning composition comprising a compound of Formula (I), or a pharmaceutically acceptable salt thereof, and a carrier suitable for use in the cleaning composition.

In yet another general aspect, the present disclosure provides a method of inhibiting conserved transcription factor σE of a bacteria, the method comprising contacting the bacteria with an effective amount of a compound of Formula (I), or a pharmaceutically acceptable salt thereof.

In yet another general aspect, the present disclosure provides a method of inhibiting virulence of a bacteria, the method comprising contacting the bacteria with an effective amount of a compound of Formula (I), or a pharmaceutically acceptable salt thereof.

In yet another general aspect, the present disclosure provides a method of killing bacteria or reducing growth of a bacteria, the method comprising contacting the bacteria with an effective amount of a compound of Formula (I), or a pharmaceutically acceptable salt thereof.

In yet another general aspect, the present disclosure provides a method of cleaning or sanitizing a surface, the method comprising contacting the surface with an effective amount of a compound of Formula (I), or a pharmaceutically acceptable salt thereof.

In yet another general aspect, the present disclosure provides a method of treating a bacterial infection, the method comprising administering to a subject in need thereof a therapeutically effective amount of a compound of Formula (I), or a pharmaceutically acceptable salt thereof.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Bacterial infections remain one of the leading causes of death worldwide. Particularly, the persistence of bacterial strains that are resistant to antibiotics poses a significant threat to human health. Described herein are inhibitors of a conserved transcription factor, $\sigma^E$, that is essential for viability or virulence in many bacterial pathogens, including Gram-negative bacterial pathogens. Compositions comprising these compounds, as well as use of these compounds as bactericidal and antibacterial agents are also described.

Therapeutic Compounds

In some embodiments, the present disclosure provides a compound of Formula (I):

(I)

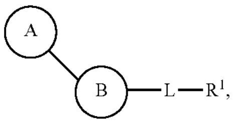

or a pharmaceutically acceptable salt thereof, wherein rings A and B, as well as L and $R^1$ are as described herein.

In some embodiments:

ring A is selected from $C_{6-10}$ aryl and $C_{3-10}$ cycloalkyl, each of which is optionally substituted with 1, 2, 3, 4, or 5 substituents independently selected from $R^A$;

ring B is selected from phenyl and pyridinyl, each of which is optionally substituted with 1, 2, 3, 4, or 5 substituents independently selected from $R^B$;

L is selected from $NR^2$, $C_{1-6}$ alkylene, —$N(R^2)C(=O)$—, —$C(=O)N(R^2)$—, —$N(R^2)S(=O)_2$—, —$S(=O)_2N(R^2)$—, S, O, C(=O), $S(=O)_2$, and 5-6-membered heteroaryl, wherein said 5-6-membered heteroaryl is optionally substituted with 1, 2, or 3 substituents independently selected from $R^3$;

$R^1$ is selected from $C_{6-10}$ aryl, 5-6-membered heteroaryl, and 4-7 membered heterocycloalkyl, each of which is optionally substituted with 1, 2, 3, 4, or 5 substituents independently selected from $R^3$;

each $R^2$ is independently selected from H, $C_{1-6}$ alkyl, $C_{1-6}$ haloalkyl, $C_{2-6}$ alkenyl, $C_{2-6}$ alkynyl, $Cy^1$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^A$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^1$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^B$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^1$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $Cy^1$ is independently selected from $C_{6-10}$ aryl, $C_{3-7}$ cycloalkyl, 5-10 membered heteroaryl, and 4-7 membered heterocycloalkyl, each of which is optionally substituted with 1, 2, 3, or 4 substituents independently selected from $R^g$;

each $R^{a1}$, $R^{b1}$, $R^{a2}$, and $R^{b2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, ring A is $C_{6-10}$ aryl, optionally substituted with 1 or 2 independently selected $R^A$.

In some embodiments, ring A is phenyl, optionally substituted with 1 or 2 independently selected $R^A$.

In some embodiments, ring A is $C_{3-10}$ cycloalkyl, optionally substituted with 1 or 2 independently selected $R^A$.

In some embodiments, ring A is cyclohexyl, optionally substituted with 1 or 2 independently selected $R^A$.

In some embodiments, ring B is phenyl, optionally substituted with 1 or 2 independently selected $R^B$.

In some embodiments, ring B is pyridinyl, optionally substituted with 1 or 2 independently selected $R^B$.

In some embodiments:

ring A is phenyl, optionally substituted with 1 or 2 independently selected $R^A$; and ring B is phenyl, optionally substituted with 1 or 2 independently selected $R^B$.

In some embodiments:

ring A is phenyl, optionally substituted with 1 or 2 independently selected $R^A$; and ring B is pyridinyl, optionally substituted with 1 or 2 independently selected $R^B$.

In some embodiments:

ring A is $C_{3-10}$ cycloalkyl (e.g., cyclohexyl), optionally substituted with 1 or 2 independently selected $R^A$; and ring B is phenyl, optionally substituted with 1 or 2 independently selected $R^B$.

In some embodiments:

ring A is $C_{3-10}$ cycloalkyl, optionally substituted with 1 or 2 independently selected $R^A$; and ring B is pyridinyl, optionally substituted with 1 or 2 independently selected $R^B$.

In some embodiments, the compound of Formula (I) has formula:

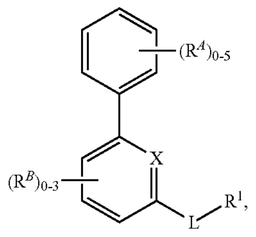

or a pharmaceutically acceptable salt thereof, wherein X is selected from N, CH, and $CR^B$.

In some embodiments, the compound of Formula (I) has formula:

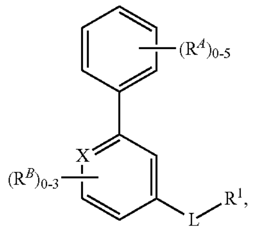

or a pharmaceutically acceptable salt thereof, wherein X is selected from N, CH, and $CR^B$.

In some embodiments, the compound of Formula (I) has formula:

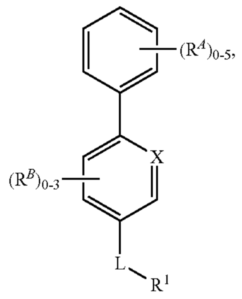

or a pharmaceutically acceptable salt thereof, wherein X is selected from N, CH, and $CR^B$.

In some embodiments, the compound of Formula (I) has formula:

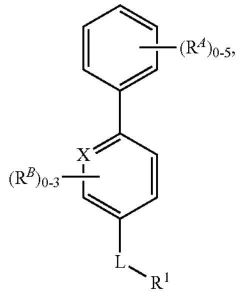

or a pharmaceutically acceptable salt thereof, wherein X is selected from N, CH, and $CR^B$.

In some embodiments, the compound of Formula (I) has formula:

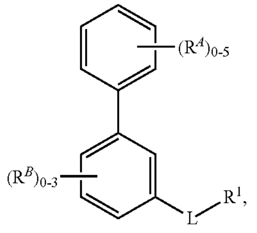

or a pharmaceutically acceptable salt thereof.

In some embodiments, the compound of Formula (I) has formula:

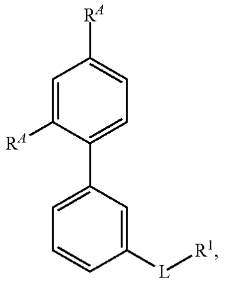

or a pharmaceutically acceptable salt thereof.

In some embodiments, the compound of Formula (I) has formula:

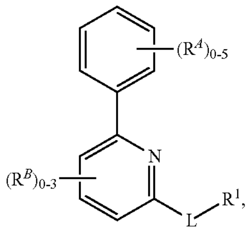

or a pharmaceutically acceptable salt thereof.

In some embodiments, the compound of Formula (I) has formula:

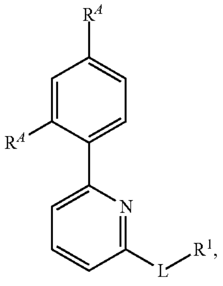

or a pharmaceutically acceptable salt thereof.

In some embodiments, L is selected from $NR^2$, $C_{1-6}$ alkylene, —$N(R^2)C(=O)$—, —$N(R^2)S(=O)_2$—, and 5-6-membered heteroaryl, wherein said 5-6-membered heteroaryl is optionally substituted with 1 or 2 substituents independently selected from $R^3$.

In some embodiments, L is $NR^2$. In some embodiments, L is NH. In some embodiments, L is —$N(R^2)C(=O)$—. In some embodiments, L is —NHC(=O)—. In some embodiments, L is —$N(R^2)S(=O)_2$—. In some embodiments, L is —$NHS(=O)_2$—.

In some embodiments, $R^2$ is selected from H, $C_{1-6}$ alkyl, $C_{1-6}$ haloalkyl, $C_{2-6}$ alkenyl, and $C_{2-6}$ alkynyl. In some embodiments, $R^2$ is H.

In some embodiments, L is $C_{1-6}$ alkylene (e.g., methylene, ethylene, or propylene).

In some embodiments, L is the 5-6-membered heteroaryl which is selected from oxadiazolyl, thiadiazolyl, thiophenyl, and triazolyl.

In some embodiments, L is the 5-6-membered heteroaryl is triazlolyl.

In some embodiments, L is a triazolyl of formula:

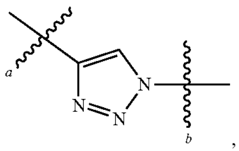 [SMILES: *c1cn(*)nn1]
, wherein a indicates a point of attachment to ring B and b indicates a point of attachment to $R^1$.

In some embodiments, the compound of Formula (I) has formula:

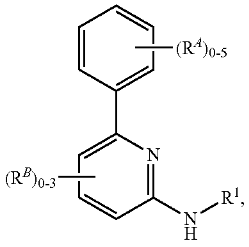

or a pharmaceutically acceptable salt thereof.

In some embodiments, the compound of Formula (I) has formula:

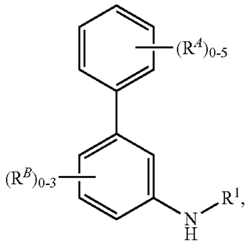

or a pharmaceutically acceptable salt thereof.

In some embodiments, the compound of Formula (I) has formula:

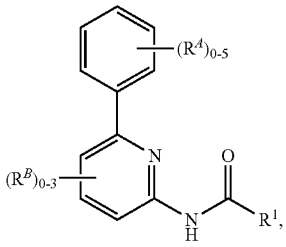

or a pharmaceutically acceptable salt thereof.

In some embodiments, the compound of Formula (I) has formula:

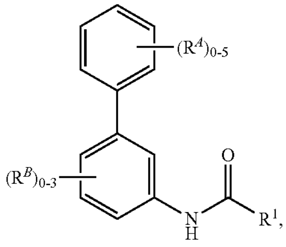

or a pharmaceutically acceptable salt thereof.

In some embodiments, the compound of Formula (I) has formula:

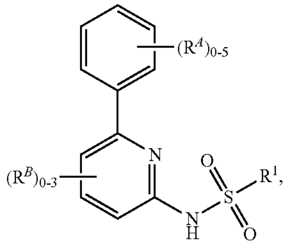

or a pharmaceutically acceptable salt thereof.

In some embodiments, the compound of Formula (I) has formula:

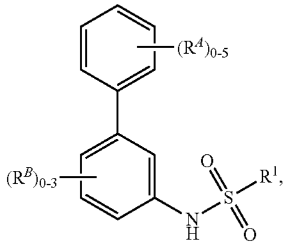

or a pharmaceutically acceptable salt thereof.

In some embodiments, the compound of Formula (I) has formula:

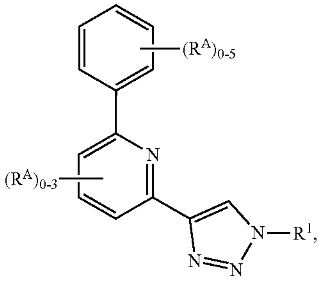

or a pharmaceutically acceptable salt thereof.

In some embodiments, the compound of Formula (I) has formula:

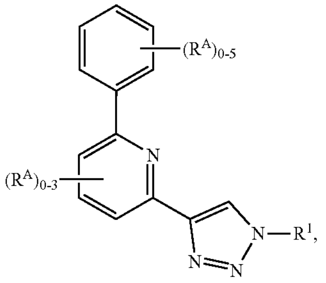

or a pharmaceutically acceptable salt thereof.

In some embodiments, $R^1$ is $C_{6-10}$ aryl, optionally substituted with 1, 2, or 3 substituents independently selected from $R^3$. In some embodiments, $R^1$ is selected from phenyl and naphthyl, each of which is optionally substituted with 1 or 2 independently selected $R^3$. In some embodiments, $R^1$ is phenyl, optionally substituted with 1 or 2 independently selected $R^3$.

In some embodiments, $R^1$ is 5-6-membered heteroaryl, optionally substituted with 1 or 2 independently selected $R^3$. In some embodiments, $R^1$ is selected from pyridinyl, benzooxadiazolyl, quinolinyl, furyl, thiophenyl, imidazolyl, and oxadiazolyl, each of which is optionally substituted with 1 or 2 independently selected $R^3$. In some embodiments, $R^1$ is pyridinyl, optionally substituted with 1 or 2 independently selected $R^3$. In some embodiments, $R^1$ is selected from quinolinyl, furyl, thiophenyl, imidazolyl, and oxadiazolyl, each of which is optionally substituted with 1 or 2 independently selected $R^3$.

In some embodiments, $R^1$ is 4-7 membered heterocycloalkyl, optionally substituted with 1 or 2 independently selected $R^3$. In some embodiments, $R^1$ is selected from tetrahydropyran, tetrahydrothiopyran, morpholinyl, and piperidinyl, each of which is optionally substituted with 1 or 2 independently selected from $R^3$.

In some embodiments, each $R^3$ is independently selected from halo, CN, $NO_2$, $C_{1-6}$ alkyl, $C_{1-6}$ haloalkyl, $C_{2-6}$ alkynyl, $N_3$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{2-6}$ alkynyl is optionally substituted with $Si(R^{b2})_3$.

In some embodiments, each $R^3$ is independently selected from halo, $NO_2$, $C_{1-6}$ alkyl, $C_{1-6}$ haloalkyl, $C_{2-6}$ alkynyl, $N_3$, $NR^{c1}R^{d1}$, and $S(O)_2R^{b1}$; wherein said $C_{2-6}$ alkynyl is optionally substituted with $Si(R^{b2})_3$.

In some embodiments, each $R^A$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl is optionally substituted with a substituent selected from $Cy^1$, $OR^{a2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$.

In some embodiments, each $R^A$ is independently selected from halo, $NO_2$, OH, $C_{1-6}$ alkyl, $C_{1-6}$ alkoxy, $C_{1-6}$ haloalkyl, and $C_{1-6}$ haloalkoxy. In some embodiments, each $R^A$ is independently selected from halo, $C_{1-6}$ alkyl, and $C_{1-6}$ haloalkyl.

In some embodiments, each $R^B$ is independently selected from halo, $C_{1-6}$ alkyl, $C_{1-6}$ haloalkyl, and $OR^{a1}$; wherein each $C_{1-6}$ alkyl is optionally substituted with a substituent selected from $Cy^1$, $OR^{a2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$.

In some embodiments, each $R^B$ is independently selected from halo, OH, $C_{1-6}$ alkyl, $C_{1-6}$ alkoxy, $C_{1-6}$ haloalkyl, and $C_{1-6}$ haloalkoxy.

In some embodiments, $Cy^1$ is $C_{6-10}$ aryl, optionally substituted with 1 or 2 independently selected from $R^g$.

In some embodiments, $Cy^1$ is $C_{3-7}$ cycloalkyl, optionally substituted with 1 or 2 independently selected from $R^g$.

In some embodiments, $Cy^1$ is 5-10 membered heteroaryl, optionally substituted with 1 or 2 independently selected from $R^g$.

In some embodiments, $Cy^1$ is 4-7 membered heterocycloalkyl, optionally substituted with 1 or 2 independently selected from $R^g$.

In some embodiments, each $R^{a1}$, $R^{b1}$, $R^{a2}$, and $R^{b2}$ is independently selected from H, $C_{1-6}$ alkyl, $C_{1-4}$haloalkyl, wherein said $C_{1-6}$ alkyl is optionally substituted with $R^g$.

In some embodiments, each $R^{c1}$, $R^{d1}$, $R^{c2}$, and $R^{d2}$ is independently selected from H, $C_{1-6}$ alkyl, $C_{1-4}$haloalkyl, wherein said $C_{1-6}$ alkyl is optionally substituted with $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments:

L is selected from $NR^2$, $C_{1-6}$ alkylene, —N($R^2$)C(═O)—, —N($R^2$)S(═O)$_2$—, and 5-6-membered heteroaryl;

each $R^2$ is independently selected from H, $C_{1-6}$ alkyl, and $C_{1-6}$ haloalkyl;

$R^1$ is selected from $C_{6-10}$ aryl, 5-6-membered heteroaryl, and 4-7 membered heterocycloalkyl, each of which is optionally substituted with 1 or 2 substituents independently selected from $R^3$;

each $R^3$ is independently selected from halo, CN, $NO_2$, $C_{1-6}$ alkyl, $C_{1-6}$ haloalkyl, $C_{2-6}$ alkynyl, $N_3$, $OR^{a1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{2-6}$ alkynyl is optionally substituted with Si($R^{b2}$)$_3$;

each $R^A$ is independently selected from halo, CN, $NO_2$, $C_{1-6}$ alkyl, $C_{1-6}$ haloalkyl, $OR^{a1}$, C(O)$R^{b1}$, C(O) $NR^{c1}R^{d1}$, C(O)$OR^{a1}$, $NR^{c1}R^{d1}$, $NR^{c1}$C(O)$R^{b1}$, $NR^{c1}$C (O)$OR^{a1}$, $NR^{c1}S(O)_2R^{b1}$, $NR^{c1}S(O)_2NR^{c1}R^{d1}$, $S(O)_2$ $R^{b1}$, and $S(O)_2NR^{c1}R^{d1}$, wherein said $C_{1-6}$ alkyl is optionally substituted with a substituent selected from $Cy^1$, $OR^{a2}$, C(O)$NR^{c2}R^{d2}$, C(O)$OR^{a2}$, $NR^{c2}R^{d2}$, $NR^{c2}$C(O)$R^{b2}$, $NR^{c2}$C(O)$OR^{a2}$, $NR^{c2}S(O)_2R^{b2}$, $NR^{c2}$S (O)$_2NR^{c2}R^{d2}$, $S(O)_2R^{b2}$, and $S(O)_2NR^{c2}R^{d2}$; and each $R^B$ is independently selected from halo, $C_{1-6}$ alkyl, $C_{1-6}$ haloalkyl, and $OR^{a1}$; wherein each $C_{1-6}$ alkyl is optionally substituted with a substituent selected from $Cy^1$, $OR^{a2}$, C(O)$NR^{c2}R^{d2}$, C(O)$OR^{a2}$, OC(O)$R^{b2}$, OC(O)$NR^{c2}R^{d2}$, $NR^{c2}R^{d2}$, $NR^{c2}$C(O)$R^{b2}$, $NR^{c2}$C(O) $OR^{a2}$, $NR^{c2}S(O)_2R^{b2}$, $S(O)_2R^{b2}$, and $S(O)_2NR^{c2}R^{d2}$.

In some embodiments:

L is selected from NH, —NHC(═O)—, —NHS(═O)$_2$—, and triazolyl;

$R^1$ is selected from phenyl, naphthyl, pyridinyl, benzooxadiazolyl, quinolinyl, furyl, and tetrahydrothiopyranyl, each of which is optionally substituted with 1 or 2 substituents independently selected from $R^3$;

each $R^3$ is independently selected from halo, $NO_2$, $C_{1-6}$ alkyl, $C_{1-6}$ haloalkyl, $C_{2-6}$ alkynyl, $N_3$, $NR^{c1}R^{d1}$, and $S(O)_2R^{b1}$; wherein said $C_{2-6}$ alkynyl is optionally substituted with Si($R^{b2}$)$_3$;

each $R^A$ is independently selected from halo, $NO_2$, OH, $C_{1-6}$ alkyl, $C_{1-6}$ alkoxy, $C_{1-6}$ haloalkyl, and $C_{1-6}$ haloalkoxy; and each $R^B$ is independently selected from halo, OH, $C_{1-6}$ alkyl, $C_{1-6}$ alkoxy, $C_{1-6}$ haloalkyl, and $C_{1-6}$ haloalkoxy.

In some embodiments, the compound of the present disclosure is selected from any one of the compounds of Table 1, or a pharmaceutically acceptable salt thereof.

In some embodiments, the compound of the present disclosure is selected from any one of the compounds of Table 2, or a pharmaceutically acceptable salt thereof.

In some embodiments, a salt (e.g., pharmaceutically acceptable salt) of a compound of Formula (I) is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula (I) include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula (I) include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formula (I), or pharmaceutically acceptable salts thereof, are substantially isolated.

Methods of Making of Antibacterial Compounds

Compounds of Formula (I), including salts thereof, can be prepared using known organic synthesis techniques and can be synthesized according to any of numerous possible synthetic routes. In some cases, compounds as provided herein are commercially available.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure,* $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* $4^{th}$ Ed., Wiley & Sons, Inc., New York (2006).

In one example, compounds of Formula (I) can be synthesized according to the methods and procedures analogous to those described in Examples 3-5, using readily available starting materials and intermediates.

Methods of Use

The compounds of Formula (I), or salt thereof, can be used in various methods. Examples of these methods include a method of inhibiting conserved transcription factor σE of a bacteria, a method of inhibiting virulence of a bacteria, a method of killing bacteria or reducing growth of a bacteria, and a method of treating or preventing a bacterial infection (e.g., an infection caused by a bacteria). These methods comprise a step of contacting the bacteria with an effective amount of a compound of Formula (I), or a pharmaceutically acceptable salt thereof.

In some embodiments, the bacteria is Gram-negative bacteria.

In some embodiments, the bacteria is a member of a family selected from the group consisting of Enterobacteriaceae, Helicobacteraceae, Campylobacteraceae, Neisseriaceae, Pseudomonadaceae, Moraxellaceae, Xanthomonadaceae, Pasteurellaceae, and Legionellaceae.

In some embodiments, the bacteria is a member of a genus selected from the group consisting of *Citrobacter, Enterobacter, Escherichia, Klebsiella, Pantoea, Proteus, Salmonella, Serratia, Shigella, Yersinia, Helicobacter, Wolinella, Campylobacter, Arcobacter, Neisseria, Francisella, Pseudomonas, Acinetobacter, Moraxella, Stenotrophomonas, Haemophilus, Pasteurella*, and *Legionella.*

In some embodiments, the bacteria is a member of *Citrobacter* genus and the species of bacteria is selected from the group consisting of *C. amalonaticus, C. braakii, C. diversus, C. farmer, C. freundii, C. gillenii, C. koseri, C. murliniae, C. rodentium, C. sedlakii, C. werkmanii*, and *C. youngae.*

In some embodiments, the bacteria is a member of *Enterobacter* genus and the species of bacteria is selected from the group consisting of *E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. ludwigii, E. mori, E. nimipressuralis, E. oryzae, E. pulveris, E. pyrinus, E. radicincitans, E. taylorae, E. turicensis, E. sakazakii*, and *E.* spp.

In some embodiments, the bacteria is a member of *Escherichia* genus and the species of bacteria is selected from the group consisting of *E. albertii, E. blattae, E. coli, E. fergusonii, E. hermannii*, and *E. vulneris.*

In some embodiments, the bacteria is a member of *Klebsiella* genus and the species of bacteria is selected from the group consisting of *K. granulomatis, K. oxytoca, K. pneumoniae, K. terrigena*, and *K. planticola.*

In some embodiments, the bacteria is a member of *Pantoea* genus and the species of bacteria is selected from the group consisting of *P. agglomerans, P. ananatis, P. citrea, P. dispersa, P. punctata, P. stewartii, P. terrea*, and *P. vagans.*

In some embodiments, the bacteria is a member of *Proteus* genus and the species of bacteria is selected from the group consisting of *P. hauseri, P. mirabilis, P. myxofaciens, P. penneri*, and *P. vulgaris.*

In some embodiments, the bacteria is a member of *Salmonella* genus and the species of bacteria is selected from the group consisting of *S. bongori*, and *S. enterica.*

In some embodiments, the bacteria is a member of *Serratia* genus and the species of bacteria is selected from the group consisting of *S. entomophila, S. ficaria, S. fonticola, S. grimesii, S. liquefaciens, S. marcescens, S. odorifera, S. plymuthica, S. proteamaculans, S. quinivorans, S. rubidaea*, and *S. symbiotica.*

In some embodiments, the bacteria is a member of *Shigella* genus and the species of bacteria is selected from the group consisting of *S. boydii, S. dysenteriae, S. flexneri*, and *S. sonnei.*

In some embodiments, the bacteria is a member of *Yersinia* genus and the species of bacteria is selected from the group consisting of *Y. pestis, Y. pseudotuberculosis*, and *Y. enterocolitica.*

In some embodiments, the bacteria is a member of *Helicobacter* genus and the species of bacteria is selected from the group consisting of *H. acinonychis, H. anseris, H. aurati, H. baculiformis, H. bilis, H. bizzozeronii, H. brantae, H. canadensis, H. canis, H. cetorum, H. cholecystus, H. cinaedi, H. cynogastricus, H. equorum, H. felis, H. fennelliae, H. ganmani, H. heilmannii, H. hepaticus, H. mesocricetorum, H. macacae, H. marmotae, H. mastomyrinus, H. mesocricetorum, H. muridarum, H. mustelae, H. pametensis, H. pullorum, H. pylori, H. rappini, H. rodentium, H. salomonis, H. suis, H. trogontum, H. typhlonius*, and *H. winghamensis.*

In some embodiments, the bacteria is a member of *Campylobacter* genus and the species of bacteria is selected from the group consisting of *C. avium, C. butzleri, C. canadensis, C. cinaedi, C. coli, C. concisus, C. corcagiensis, C. cryaerophilus, C. cuniculorum, C. curvus, C. fennelliae, C. fetus, C. gracilis, C. helveticus, C. hominis, C. hyoilei, C. hyointestinalis, C. insulaenigrae, C. jejuni, C. lanienae, C. lari, C. mucosalis, C. mustelae, C. nitrofigilis, C. peloridis, C. pylori, C. rectus, C. showae, C. sputorum, C. subantarcticus, C. upsaliensis, C. ureolyticus*, and *C. volucris.*

In some embodiments, the bacteria is a member of *Arcobacter* genus and the species of bacteria is selected from the group consisting of *A. bivalviorum, A. butzleri, A. cibarius, A. cryaerophilus, A. defluvii, A. ellisii, A. halophilus, A. marinus, A. molluscorum, A. mytili, A. nitrofigilis, A. skirrowii, A. thereius, A. trophiarum*, and *A. venerupis.*

In some embodiments, the bacteria is a member of *Neisseria* genus and the species of bacteria is selected from the group consisting of *N. bacilliformis, N. cinerea, N. denitrificans, N. elongata, N. flavescens, N. gonorrhoeae, N. lactamica, N. macacae, N. meningitidis, N. mucosa, N. pharyngis, N. polysaccharea, N. sicca, N. subflava*, and *N. weaver.*

In some embodiments, the bacteria is a member of *Francisella* genus and the species of bacteria is selected from the group consisting of *F. tularensis, F. novicida, F. hispaniensis, W. persica, F. noatunensis, F. philomiragia, F. halioticida, F. endociliophora*, and *F. guangzhouensis.*

In some embodiments, the bacteria is a member of *Pseudomonas* genus and the species of bacteria is selected from the group consisting of *P. aeruginosa, P. oryzihabitans*, and *P. plecoglossicida.*

In some embodiments, the bacteria is a member of *Acinetobacter* genus and the species of bacteria is *A. baumannii.*

In some embodiments, the bacteria is a member of *Moraxella* genus and the species of bacteria is selected from the group consisting of *M. catarrhalis, M. lacunata*, and *M. bovis.*

In some embodiments, the bacteria is a member of *Stenotrophomonas* genus and the species of bacteria is *S. maltophilia.*

In some embodiments, the bacteria is a member of *Haemophilus* genus and the species of bacteria is selected from the group consisting of *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus.*

In some embodiments, the bacteria is a member of *Pasteurella* genus and the species of bacteria is selected from the group consisting of *P. multocida, P. stomatis, P. dagmatis, P. canis, P. bettyae*, and *P. anatis.*

In some embodiments, the bacteria is a member of *Legionella* genus and the species of bacteria is selected from the group consisting of *L. pneumophila, L. anisa, L. bozemanae, L. cincinnatiensis, L. gormanii, L. jordani, L. longbeachae, L. maceachernii, L. micdadei, L. sainthelensi, L. wadsworthii*, and *L. waltersii.*

In some embodiments, the bacteria is a member of *Mycobacterium* genus and the species of bacteria is selected from a group consisting of *M. tuberculosis* and *M. smegmatic.*

In some embodiments, the bacteria is a member of a genus selected from: *Acinetobacter, Burkholderia, Acinetobacter, Burkholderia, Klebsiella, Pseudomonas*, and *Escherichia*. In such embodiments, the bacteria is a member of a species selected from: *K. pneumoniae, P aeruginosa*, Enterobacteriaceae, and *E. coli.*

In some embodiments, the bacteria is Gram-positive bacteria.

In some embodiments, the bacteria is a member of a genus selected from the group consisting of *Staphylococcus* (including coagulase negative and coagulase positive), *Streptococcus, Peptococcus, Enterococcus*, and *Bacillus.*

In some embodiments, the bacteria is a member of *Staphylococcus* genus and the species of bacteria is selected from the group consisting of *S. aureus, methicillin-susceptible S. aureus* (MSSA), coagulase negative staphylococci, methicillin-resistant *S. aureus* (MRSA), vancomycin-resistant *S. aureus* (VRSA), *S. arlettae, S. agnetis, S. auricularis, S. capitis, S. caprae, S. carnosus, S. caseolyticus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus.*

In some embodiments, the bacteria is a member of *Peptococcus* genus and the species of bacteria is *P. magnus.*

In some embodiments, the bacteria is a member of *Streptococcus* genus and the species of bacteria is selected from the group consisting of *S. agalactiae, S. anginosus, S. bovis, S. canis, S. constellatus, S. dysgalactiae, S. equinus, S. iniae, S. intermedius, S. milleri, S. mitis, S. mutans, S. oralis, S. parasanguinis, S. peroris, S. pneumoniae, S. pseudopneumoniae, S. pyogenes, S. ratti, S. salivarius, S. tigurinus, S. thermophilus, S. sanguinis, S. sobrinus, S. suis, S. uberis, S. vestibularis, S. viridans*, and *S. zooepidemicus.*

In some embodiments, the bacteria is a member of *Enterococcus* genus and the species of bacteria is selected from the group consisting of *E. avium, E. durans, E. faecalis, E. gallinarum, E. haemoperoxidus, E. hirae, E. malodoratus, E. moraviensis, E. mundtii, E. pseudoavium, E. raffinosus, E. solitaries*, and *E. faecium.*

In some embodiments, the bacteria is a member of *Propionibacterium* genus. In such embodiments, the bacteria is *P. acnes.*

In some embodiments, the bacterial infection treatable by the compounds of the present disclosure is caused by any one of the bacteria described herein (e.g., *E. coli*, or MRSA). In some embodiments, the bacterial infection is resistant to treatment with one or more of the antibiotic agents described herein (e.g., bacterial infection is resistant to treatment with methicillin, vancomycin, rifampicin, gentamicin and/or ciprofloxacin). In these embodiments, the bacterial infection is characterized as persistent to treatment with one or more available antibiotic agents.

In some embodiments, the bacterial infection is a skin infection. In some aspects of these embodiments, the skin infection is selected from the group consisting of acne, pimples, impetigo, boils, cellulitis, folliculitis, carbuncles, scalded skin syndrome, skin abscesses, atopic dermatitis, and typhoid fever. In such embodiments, the skin infection is acne. In some embodiments, the bacterial infection is a skin and soft tissue infection (e.g., acne).

In some embodiments, the bacterial infection is a respiratory infection. In some aspects of these embodiments, the respiratory infection is selected from the group consisting of upper respiratory tract infection, bronchopneumonia, atypical pneumonia, tuberculosis, *Mycobacterium tuberculosis*, pneumonia, anaerobic pleuropulmonary infection, ventilator-associated pneumonia, aspiration pneumonia, lung abscess, bronchitis, chronic obstructive pulmonary disease, obstructive pulmonary disease, Pontiac fever, and legionellosis.

In some embodiments, the bacterial infection is a wound infection. In some aspects of these embodiments, the wound infection is a postsurgical wound infection.

In some embodiments, the bacterial infection is a blood stream infection. In some aspects of these embodiments, the blood stream infection is bacteremia or sepsis. In some embodiments, the bacterial infection is a pelvic infection. In some aspects of the embodiments, the pelvic infection is bacterial vaginosis.

In some embodiments, the bacterial infection is a gastrointestinal infection. In some aspects of these embodiments, the gastrointestinal infection is selected from the group consisting of peptic ulcer, chronic gastritis, duodenitis, gastroenteritis, diarrhea, dysentery, diphtheria, food poisoning and foodborne illness.

In some embodiments, the bacterial infection is a bone, joint or muscle infection. In some aspects of these embodiments, the bone, joint or muscle infection is selected from the group consisting of tetanus, secondary meningitis, meningitis, neonatal meningitis, sinusitis, laryngitis, arthritis, septic arthritis, Bartholin gland abscess, chancroid, osteomyelitis, endocarditis, mediastinitis, pericarditis, peritonitis, otitis media, blepharoconjunctivitis, keratoconjunctivitis, and conjunctivitis.

In some embodiments, the bacterial infection is selected from the group consisting of a dental infection, a zoonotic infection, an invasive systemic infection, a urinary tract infection, an abdominal infection, a CNS infection, an endovascular infection, and a nosocomial infection. In some embodiments, the bacterial infection is selected from the group consisting of syphilis, leprosy, abscesses, sepsis, empyema, and tularemia.

In some embodiments, the bacterial infection is associated with implanted devices (e.g., catheter, balloon catheter, stent, pacer, etc.). In some embodiments, the bacterial infection is osteomyelitis, endocarditis, or an infection associated with an implanted device.

In some embodiments, the bacterial infection is a connective tissue infection, or a joint or muscle infection. In such embodiments, the joint infection is an infection of a shoulder, a knee, a hip, or an elbow. In some embodiments, the bacterial infection is septic arthritis.

Cleaning Compositions

In some embodiments, any one of compounds of Formula (I), or a salt thereof, may be used for killing bacteria on a surface (e.g., for disinfecting or sanitizing a surface). The surface may be metallic, plastic, ceramic, or wooden, for example, the surface is a floor, a table, a kitchen counter, a cutting board, or a medical instrument. Hence, any one of the compounds of the present application may be used in a commercial setting for general disinfecting, e.g., in medical and food industries. For these purposes, the compound may be provided in a cleaning composition comprising an acceptable carrier. The carrier(s) are "acceptable" in the sense of being compatible with the other ingredients of the cleaning composition. Acceptable carriers that may be used in a cleaning composition of the present application include, but are not limited to, alcohols, water, surfactants, emollients, stabilizers, thickeners, viscosifiers, and fragrances.

Additional Therapeutic Agents

In some embodiments, a composition or a method of the present application further comprises using one or more additional therapeutic agents. The additional therapeutic agent may be selected from any compound or therapeutic agent known to have or that demonstrates advantageous properties when administered with a compound of the present disclosure. The additional therapeutic agent may be administered to the subject in a separate pharmaceutical composition or dosage form (e.g., any one of the compositions, formulation, routes and dosage forms described herein). In these embodiments, a compound as provided herein, or a pharmaceutically acceptable salt thereof, can be used in combination with an antibiotic.

In some embodiments, a compound as provided herein, or a pharmaceutically acceptable salt thereof, can be used in combination with a cationic antimicrobial peptide (CAMP). In some aspects of these embodiments, the cationic antimicrobial peptide is a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), or drosomycin (e.g., from fruit flies).

In some embodiments, the antibiotic is selected from the quinolone class of antibiotic compounds. In some aspects of these embodiments, the antibiotic is selected from the group consisting of levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

In some embodiments, the antibiotic is selected from a β-lactam, a monobactam, oxazolidinone, and lipopeptide.

In some embodiments, the antibiotic is selected from the cephalosporin class of antibiotic compounds. In some aspects of these embodiments, the antibiotic is selected from the group consisting of cefazolin, cefuroxime, ceftazidime, cephalexin, cephaloridine, cefamandole, cefsulodin, cefonicid, cefoperazine, cefoprozil, and ceftriaxone.

In some embodiments, the antibiotic is selected from the penicillin class of antibiotic compounds. In some aspects of these embodiments, the antibiotic is selected from the group consisting of penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

In some embodiments, the antibiotic is selected from the carbapenem class of antibiotic compounds. In some aspects of these embodiments, the antibiotic is selected from the group consisting of thienamycin, tomopenem, lenapenem, tebipenem, razupenem, imipenem, meropenem, ertapenem, doripenem, panipenem (betamipron), and biapenem.

In some embodiments, the antibiotic is selected from the lipopeptide class of antibiotic compounds. In some aspects of these embodiments, the antibiotic is selected from the group consisting of polymyxin B, colistin (polymyxin E), and daptomycin.

In some embodiments, the antibiotic is selected from the aminoglycoside class of antibiotic compounds. In some aspects of these embodiments, the antibiotic is selected from the group consisting of gentamicin, amikacin, tobramycin, debekacin, kanamycin, neomycin, netilmicin, paromomycin, sisomycin, spectinomycin, and streptomycin.

In some embodiments, the antibiotic is selected from the glycopeptide class of antibiotic compounds. In some aspects of these embodiments, the antibiotic is selected from the group consisting of vancomycin, teicoplanin, telavancin, ramoplanin, daptomycin, decaplanin, and bleomycin.

In some embodiments, the antibiotic is selected from the macrolide class of antibiotic compounds. In some aspects of these embodiments, the antibiotic is selected from the group consisting of azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

In some embodiments, the antibiotic is selected from the ansamycin class of antibiotic compounds. In some aspects of these embodiments, the antibiotic is selected from the group consisting of streptovaricin, geldanamycin, herbimycin, rifamycin, rifampin, rifabutin, rifapentine and rifamixin.

In some embodiments, the antibiotic is selected from the sulfonamide class of antibiotic compounds. In some aspects of these embodiments, the antibiotic is selected from the group consisting of sulfanilamide, sulfacetamide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

In some embodiments, the antibiotic is selected from the group consisting of quinolones, fluoroquinolones, β-lactams, cephalosporins, penicillins, carbapenems, lipopeptide antibiotics, glycopeptides, macrolides, ansamycins, sulfonamides, and combinations of two or more thereof.

In some embodiments, the present application provides separate dosage forms of a compound described herein, or a pharmaceutically acceptable salt thereof, and one or more of any of the above-described second therapeutic agents. The separate dosage forms may be administered together consecutively (e.g., within less than 24 hours of one another) or simultaneously (e.g., administered to the patient within 5 minutes of one another).

Pharmaceutical Compositions

In some embodiments, the present application also provides pharmaceutical compositions comprising an effective amount of a compound of Formula (I), or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. In certain embodiments, the compound of Formula (I) herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compound of Formula (I), or a pharmaceutically acceptable salt thereof, is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application (e.g., skin and soft tissues).

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form, as a cream or a paste.

In some embodiments, the topical composition comprises a combination of a compound of Formula (I), or a pharmaceutically acceptable salt thereof, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof). In some embodiments, suitable carriers include, but are not limited to, mineral oil, sorbitan monostearate, polysorbate 60, cetyl esters wax, cetearyl alcohol, 2-octyldodecanol, benzyl alcohol, and water. In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and styrax benzoin. In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate. In some embodiments, sunscreen actives may include, but are not limited to, avobenzone, benzephenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate O, para-aminobenzoic acid (PABA), Parsol 1789, terephthalylidine dicamphor sulfonic acid, Tinosorb M, Tinosorb S, and titanium dioxide. In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 poly dimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, *Salvia officinalis, Saponaria officinalis* extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

Application of the subject therapeutics may be local, so as to be administered at the site of interest (e.g., infected area of skin, or an infected joint or other connective tissue). Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application.

Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In the pharmaceutical compositions of the present application, a compound of Formula (I), or a pharmaceutically available salt thereof, is present in an effective amount (e.g., a therapeutically effective amount).

In some embodiments, an effective amount of a compound of Formula (I), or a pharmaceutically acceptable salt thereof, can range, for example, from about 1 mg to about 200 mg, from about 1 mg to about 100 mg, from about 1 mg to about 50 mg, from about 1 mg to about 30 mg, from about 1 mg to about 15 mg, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some embodiments, an effective amount of a compound of Formula (I), or a pharmaceutically acceptable salt thereof, is 1 mg, 2 mg, 3 mg, 4 mg, 5 mg, 6 mg, 7 mg, 8 mg, 9 mg, or 10 mg. In some aspects of these embodiments, the composition containing an effective amount of a compound of Formula (I), or a pharmaceutically acceptable salt thereof, is administered once daily. In some aspects of these embodiments, the composition containing an effective amount of a compound of Formula (I), or a pharmaceutically acceptable salt thereof, is administered twice daily. In some aspects of these embodiments, the composition containing an effective amount of a compound of Formula (I), or a pharmaceutically acceptable salt thereof, is administered thrice daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, butyl, pentyl, and hexyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridinyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula $—NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms. As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —C(O)NH$_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C═O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, N═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the σE with a compound of the invention includes the administration of a compound of the present invention to an individual or patient, such as a human, having σE, as well as, for example, introducing a compound of the invention into a sample containing a cellular or purified preparation containing the σE.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

EXAMPLES

Example 1—Chemical Structures of Exemplified Tested Compounds

TABLE 1

| No. | Structure | No. | Structure |
| --- | --- | --- | --- |
| 2170 | 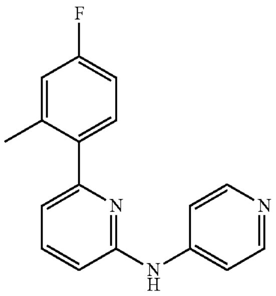 | 39732 | 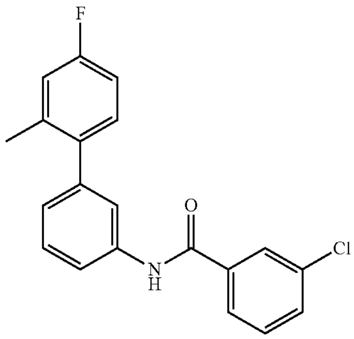 [SMILES: Cc1cc(F)ccc1-c1cccc(NC(=O)c2cccc(Cl)c2)c1] |
| 39711 | 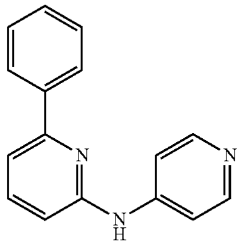 [SMILES: c1ccc(-c2cccc(Nc3ccncc3)n2)cc1] | 39724 | 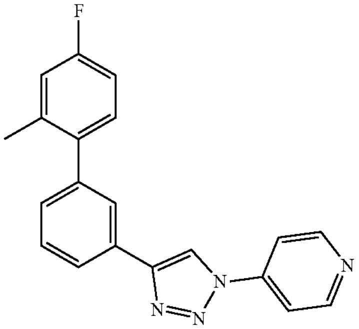 [SMILES: Cc1cc(F)ccc1-c1cccc(-c2cn(-c3ccncc3)nn2)c1] |
| 39744 | 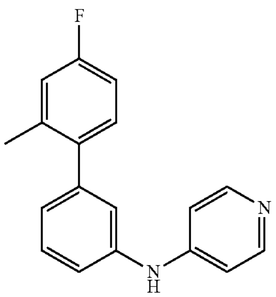 [SMILES: Cc1cc(F)ccc1-c1cccc(Nc2ccncc2)c1] | 39720 | 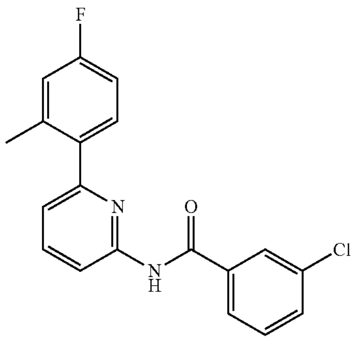 [SMILES: Cc1cc(F)ccc1-c1cccc(NC(=O)c2cccc(Cl)c2)n1] |

TABLE 1-continued
| No. | Structure | No. | Structure |
|---|---|---|---|
| 39704 | 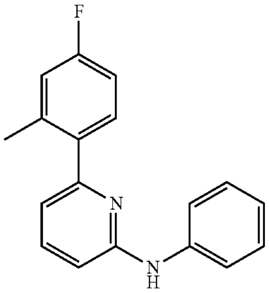 [SMILES: Cc1cc(F)ccc1-c1cccc(Nc2ccccc2)n1] | 39748 | 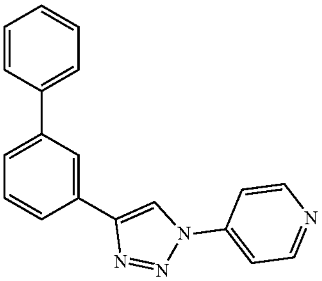 [SMILES: c1ccc(-c2cccc(-c3cn(-c4ccncc4)nn3)c2)cc1] |
| 39731 | 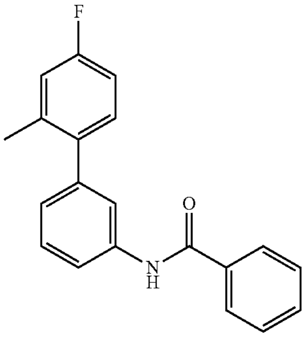 [SMILES: Cc1cc(F)ccc1-c1cccc(NC(=O)c2ccccc2)c1] | 39751 | 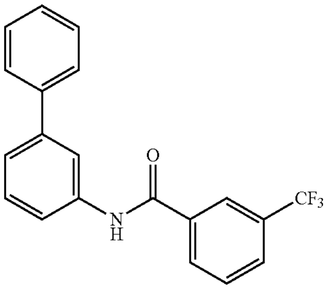 [SMILES: O=C(Nc1cccc(-c2ccccc2)c1)c1cccc(C(F)(F)F)c1] |
Example 2—Chemical Structures of Exemplified Tested Compounds
TABLE 2
| No. | Structure | No. | Structure |
|---|---|---|---|
| 39710 | 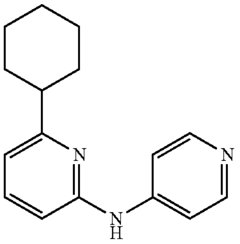 [SMILES: c1cc(Nc2ccncc2)nc(C2CCCCC2)c1] | 39721 | 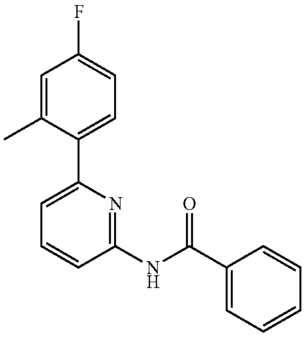 [SMILES: Cc1cc(F)ccc1-c1cccc(NC(=O)c2ccccc2)n1] |

TABLE 2-continued
| No. | Structure | No. | Structure |
|---|---|---|---|
| 39718 | 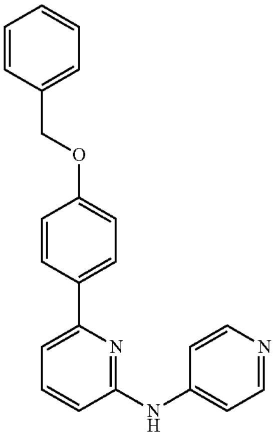 [SMILES: c1ccc(COc2ccc(-c3cccc(Nc4ccncc4)n3)cc2)cc1] | 39712 | 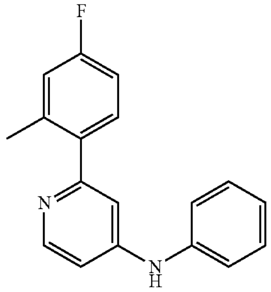 [SMILES: Cc1cc(F)ccc1-c1cc(Nc2ccccc2)ccn1] |
| 39709 | 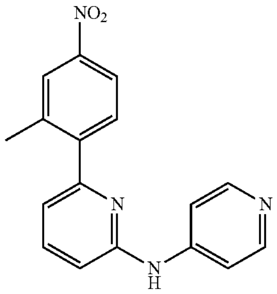 [SMILES: Cc1cc([N+](=O)[O-])ccc1-c1cccc(Nc2ccncc2)n1] | 39730 | 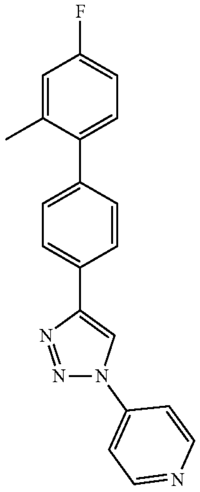 [SMILES: Cc1cc(F)ccc1-c1ccc(-c2cn(-c3ccncc3)nn2)cc1] |
| 39722 | 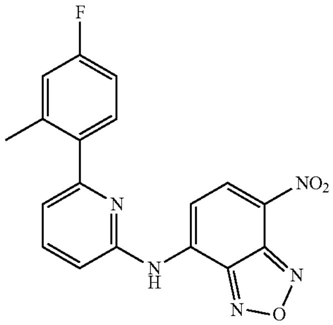 [SMILES: Cc1cc(F)ccc1-c1cccc(Nc2ccc([N+](=O)[O-])c3nonc23)n1] | 39717 | 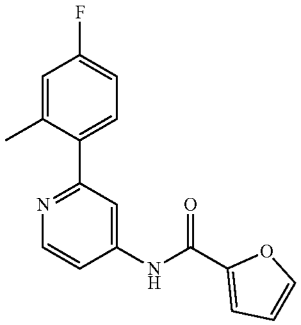 [SMILES: Cc1cc(F)ccc1-c1cc(NC(=O)c2ccco2)ccn1] |
| 39705 | 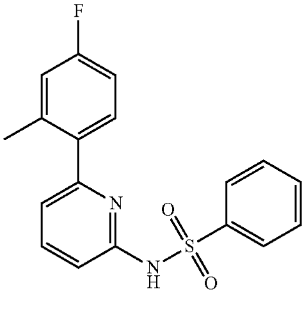 [SMILES: Cc1cc(F)ccc1-c1cccc(NS(=O)(=O)c2ccccc2)n1] | 39733 | 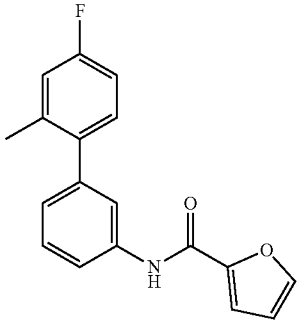 [SMILES: Cc1cc(F)ccc1-c1cccc(NC(=O)c2ccco2)c1] |

TABLE 2-continued
| No. | Structure | No. | Structure |
|---|---|---|---|
| 39713 | 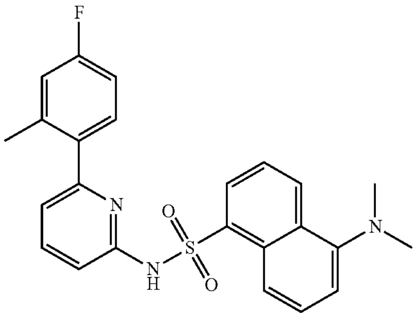 | 39734 | 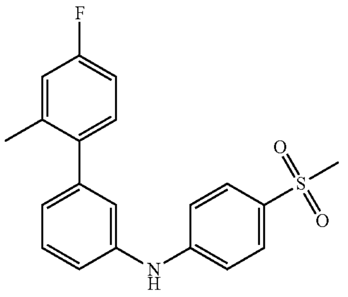 |
| 39714 | 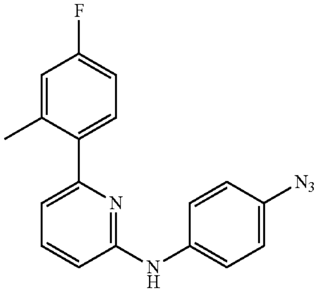 [SMILES: Cc1cc(F)ccc1-c1cccc(Nc2ccc(N=[N+]=[N-])cc2)n1] | 39735 | 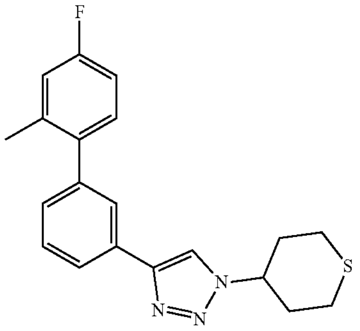 [SMILES: Cc1cc(F)ccc1-c1cccc(-c2cn(C3CCSCC3)nn2)c1] |
| 39715 | 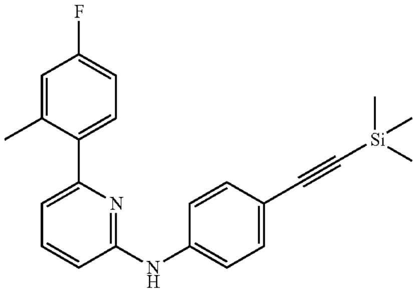 | 39739 | 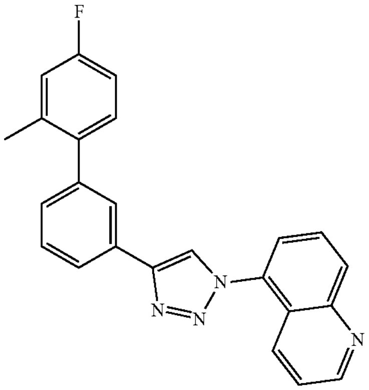 [SMILES: Cc1cc(F)ccc1-c1cccc(-c2cn(-c3cccc4ncccc34)nn2)c1] |
Example 3—Chemical Synthesis of Compounds 39704 and 39720
Synthesis of Intermediate Compound X (6-(4-fluoro-2-methylphenyl)pyridin-2-amine)
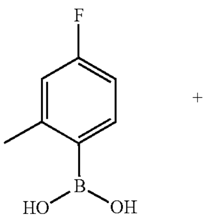
-continued
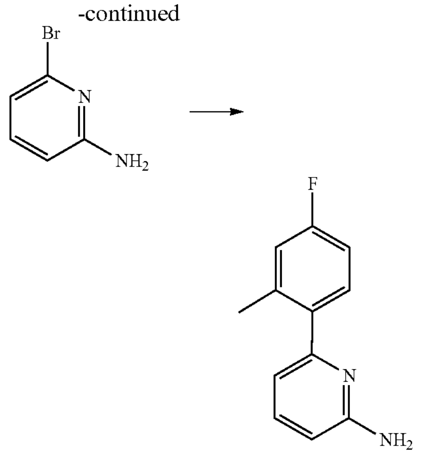
4-fluoro-2-methylphenyl)boronic acid (1 eq), 6-bromopyridin-2-amine (1 eq), $Pd(dppf)Cl_2$ (0.05 eq) and $Cs_2CO_3$ (2.5 eq) were added to a flask containing 8 ml of a degassed solution of tetrahydrofuran/water (4:1, v/v). The flask was fit with a condenser and transferred to a pre-heated oil bath maintained at 80-90° C. The reaction mixture was allowed to reflux for 24 h while monitoring by TLC. After 24 h, the reaction was quenched by adding 20 ml of water and extracted three times with 60 ml of dichloromethane. The combined organic phase was dried with anhydrous sodium sulfate and concentrated under reduced pressure. The crude product was purified over silica gel with 30% ethyl acetate in hexanes to give 6-(4-fluoro-2-methylphenyl) pyridin-2-amine (1.2 g of a beige solid) as the product in 86% yield. $^1H$-NMR ($CDCl_3$, 400 MHz): δ 2.33 (s, 3H), 4.29 (bs, 2H), 6.50 (d, J=8.0 Hz, 1H), 6.57 (s, 1H), 6.89-6.98 (m, 2H), 7.22-7.33 (m, 1H), 8.26 (d, J=8.0 Hz, 1H).

Synthesis of Compound 39704

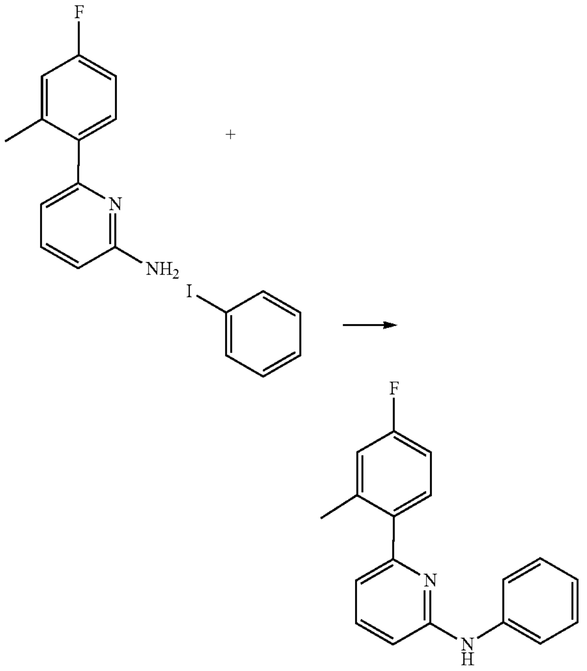

6-(4-fluoro-2-methylphenyl)pyridin-2-amine (1 eq), iodobenzene (1 eq), $Pd_2(dba)_3$ (0.125 eq). SPhos (0.25 eq) and $Cs_2CO_3$ (2 eq) were added to a flask containing anhydrous toluene (8 ml) and a stir bar. The flask was fit with a condenser and transferred to a pre-heated oil bath maintained at 120° C. The reaction mixture was allowed to reflux for 24 h while monitoring by TLC. After 24 h, the reaction was quenched by adding 20 ml of water and extracted three times with 80 ml of dichloromethane. The organic phase was dried with anhydrous sodium sulfate and concentrated under reduced pressure. The crude product was purified by column chromatography over silica gel eluting with 2% methanol in dichloromethane to give a brownish powder. $^1H$-NMR ($CDCl_3$, 400 MHz): δ 2.40 (s, 3H), 6.70 (s, 1H), 6.79 (d, J=8.0 Hz, 1H), 6.86 (d, J=8.0 Hz, 1H), 6.91-7.00 (m, 2H), 7.00-7.09 (m, 1H), 7.29-7.33 (m, 3H), 7.35-7.42 (m, 1H), 7.54 (t, J=8.0 Hz, 1H). $^{13}C$-NMR ($CDCl_3$, 100 MHz): δ 20.8, 106.1, 112.6, 112.8, 115.5, 117.2, 117.4, 122.9, 129.4, 131.3, 136.8, 138.1, 138.6, 140.7, 155.5, 158.1, 161.3, 163.8.

Synthesis of Compound 39720

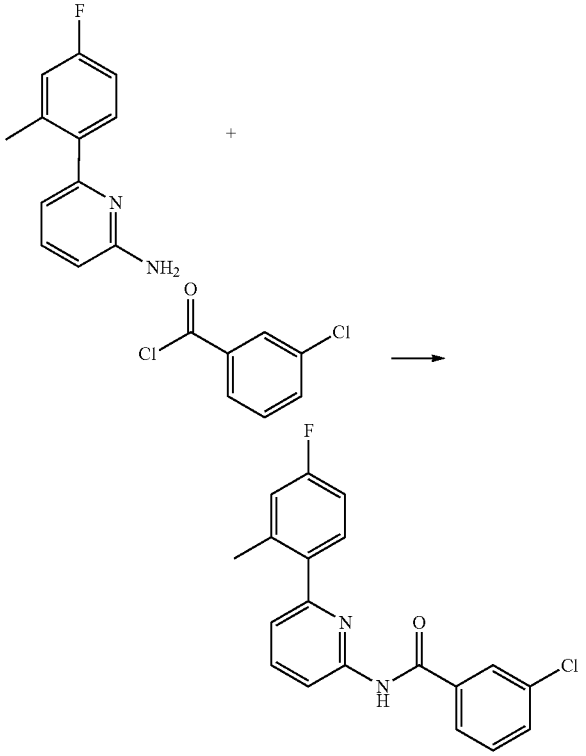

6-(4-fluoro-2-methylphenyl)pyridin-2-amine (1 eq) was added to a dry flask containing triethylamine (3 eq) dissolved in 5 ml of dichloromethane at room temperature. The flask was sealed and purged with Argon gas. 3-Chlorobenzoyl chloride (1.1 eq) was then added slowly to the reaction flask while stirring the mixture. The reaction was then allowed to proceed at room temperature for 24 h. After 24 h, the reaction mixture was evaporated under reduced pressure and the crude product was purified by column chromatography over silica gel eluting with 15-20% ethyl acetate in hexanes to give a white powder in quantitative yields. $^1H$-NMR ($CDCl_3$, 400 MHz): δ 2.34 (s, 3H), 6.92-7.02 (m, 2H), 7.15 (d, J=8.0 Hz, 1H), 7.29-7.36 (m, 1H), 7.42 (t, J=8.0 Hz, 1H), 7.53 (d, J=8.0 Hz, 1H), 7.77 (d, J=8.0 Hz, 1H), 7.84 (t, J=8.0 Hz, 1H), 7.88-7.92 (m, 1H), 8.34 (d, J=8.0 Hz, 1H), 8.66 (s, 1H). $^{13}C$-NMR ($CDCl_3$, 100 MHz): δ 20.6, 112.4, 112.9, 113.1, 117.4, 117.6, 120.7, 125.3, 127.8, 130.3, 131.2, 131.2 132.4, 135.3, 136.1, 139.1, 150.8, 157.8, 164.5.

Example 4—Chemical Synthesis of Compound 39724

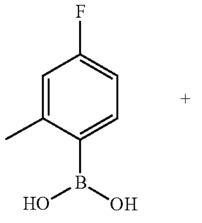

-continued

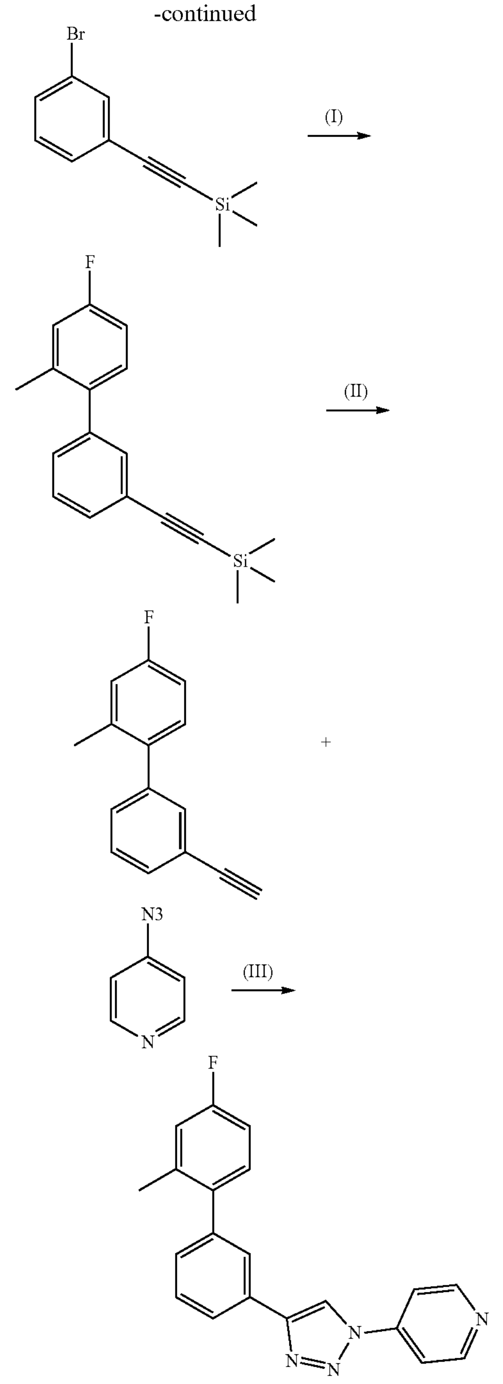

Step I: (4-fluoro-2-methylphenyl)boronic acid (1 eq.), ((3-bromophenyl)ethynyl) trimethylsilane (1.2 eq.), Pd(dppf)$Cl_2$ (0.05 eq.) and $Cs_2CO_3$ (2.5 eq.) were added to a flask containing 8 ml of a degassed solution of tetrahydrofuran/water (4:1, v/v). The flask was fit with a condenser and transferred to a pre-heated oil bath maintained at 80-90° C. The reaction was allowed to reflux for 24 h and monitored by TLC. After 24 h, the reaction was quenched by adding 30 ml of water and extracted three times with 60 ml of dichloromethane. The combined organic phase was dried with anhydrous magnesium sulfate and concentrated under reduced pressure. The crude product was purified over silica gel with 100% hexanes to give a clear oil in 86% yield.

Step II: TMS deprotection was performed by taking ((4'-fluoro-2'-methyl-[1,1'-biphenyl]-3-yl)ethynyl)trimethylsilane (1 eq) and dissolving it in 5 ml of a 1:1 (v/v) solution of THF/MeOH. $K_2CO_3$ (10 eq) was then added to the flask and the reaction was stirred at room temperature overnight (~12 h). The reaction was then concentrated in vacuo and purified over silica gel eluting with 100% hexanes to give a clear oil in quantitative yields. $^1$H-NMR ($CDCl_3$, 400 MHz): δ 2.28 (s, 3H), 3.31 (s, 1H), 6.92-7.05 (m, 2H), 7.19 (t, J=8.0 Hz, 1H), 7.30 (d, J=8.0 Hz, 1H), 7.40 (t, J=8.0 Hz, 1H), 7.46 (s, 1H), 7.52 (d, J=8.0 Hz, 1H).

Step III: 3'-ethynyl-4-fluoro-2-methyl-1,1'-biphenyl (1.1 eq), 4-azidopyridine (1 eq), copper sulfate (0.01 eq), THPTA (0.02 eq) and sodium ascorbate (0.02 eq) were combined in a 50 ml flask containing a solution of 40% acetonitrile in water at room temperature. The reaction was stirred overnight and water (30 ml) was then added. A white precipitate was isolated by vacuum filtration and purified over silica gel with an ethyl acetate/hexanes mixture (10:90%) to give compound KKL-39724 in quantitative yield. $^1$H-NMR ($CDCl_3$, 400 MHz): δ 2.31 (s, 3H), 6.34-7.06 (m, 2H), 7.22-7.30 (m, 1H), 7.34 (d, J=8.0 Hz, 1H), 7.54 (t, J=8.0 Hz, 1H), 7.81 (dd, J=4.0 Hz, J=8.0 Hz, 2H), 7.86 (s, 1H), 7.92 (d, J=8.0 Hz, 1H), 8.35 (s, 1H), 8.83 (dd, J=4.0 Hz, J=8.0 Hz, 2H). $^{13}$C-NMR ($CDCl_3$, 100 MHz): δ 20.6, 112.7, 113.7, 116.8, 116.9, 124.6, 126.9, 128.9, 129.6, 129.8, 131.2, 137.3, 137.8, 141.9, 143.0, 149.0, 151.8.

Example 5—Chemical Synthesis of Compounds 39731, 39732, and 39733

Synthesis of Intermediate Compound Y (4'-fluoro-2'-methyl-[1,1'-biphenyl]-3-amine)

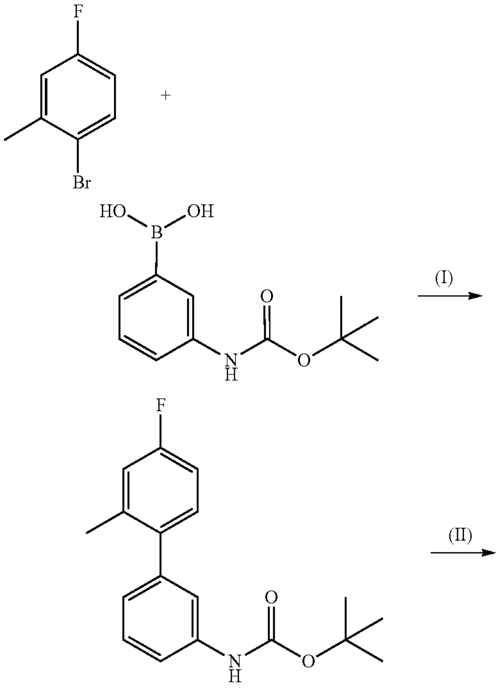

-continued

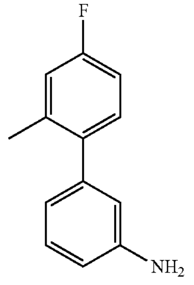

Step I: 1-bromo-4-fluoro-2-methylbenzene (1 eq), $Pd(dppf)Cl_2$ (0.05 eq), $Cs_2CO_3$ (2.5 eq) and (3-((tert-butoxy-carbonyl)amino)phenyl)boronic acid (1.2 eq) were transferred to a flask containing a 4:1 solution of $THF:H_2O$ (v/v). The flask was fit with a condenser and transferred to a pre-heated oil bath maintained at 80-90° C. The reaction was allowed to reflux for 24 h and monitored by TLC. After 24 h, the reaction was quenched by adding 30 ml of water and extracted three times with 60 ml of dichloromethane. The combined organic phase was dried with anhydrous magnesium sulfate and concentrated under reduced pressure. The crude was purified over silica gel and eluted with 20% ethyl acetate in hexanes. The obtained product was used directly in the BOC deprotection procedure below.

Step I: tert-butyl (4'-fluoro-2'-methyl-[1,1'-biphenyl]-3-yl)carbamate (3.79 eq) was added to a flask containing a 1:1 solution of dichloromethane and trifluoroacetic acid. This reactions was stirred overnight at room temperature. Volatile solvents were then evaporated under reduced pressure. The crude material was purified over silica gel and eluted with 30% ethyl acetate in hexanes to give the pure product in 76% yield. $^1$H-NMR ($CDCl_3$, 400 MHz): δ 2.35 (s, 3H), 4.31 (bs, 2H), 6.37-6.60 (m, 2H), 6.79-7.01 (m, 2H), 7.15-7.35 (m, 2H), 8.24 (d, J=8.0 Hz, 1H).

Synthesis of Compound 39731

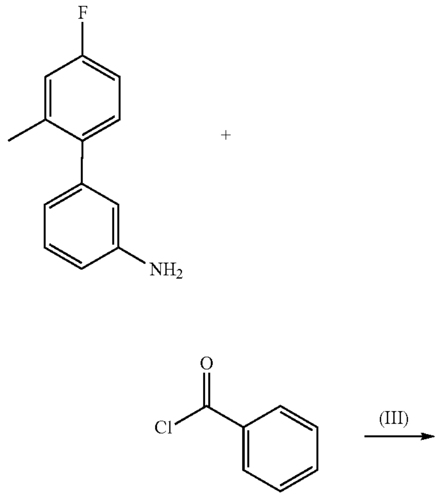

-continued

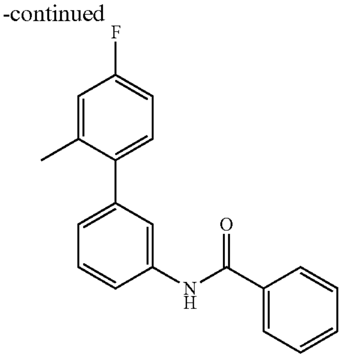

4'-fluoro-2'-methyl-[1,1'-biphenyl]-3-amine (1 eq) was added to a dry flask containing triethylamine (3 eq) dissolved in 5 ml of dichloromethane at room temperature. The flask was sealed and purged with Argon gas. Benzoyl chloride (1.1 eq) was then added slowly to the reaction flask while stirring the mixture. The reaction was then allowed to proceed at room temperature for 24 h. After 24 h, the reaction mixture was evaporated under reduced pressure and the crude product was purified by column chromatography over silica gel eluting with 15-20% ethyl acetate in hexanes to give a white powder in quantitative yield. $^1$H-NMR ($CDCl_3$, 400 MHz): δ 2.30 (s, 3H), 6.89-7.02 (m, 2H), 7.09 (d, J=8.0 Hz, 1H), 7.17-7.23 (m, 1H), 7.41 (t, J=8.0 Hz, 1H), 7.45-7.52 (m, 2H), 7.53-7.59 (m, 1H), 7.60-7.68 (m, 2H), 7.89 (d, J=8.0 Hz, 2H), 8.05 (s, 1H). $^{13}$C-NMR ($CDCl_3$, 100 MHz): δ 20.7, 112.5, 112.7, 116.8, 117.0, 119.0, 121.3, 125.7, 127.2, 129.0, 131.2, 132.0, 153.0, 137.9, 142.1, 160.9, 163.4, 166.0.

Synthesis of Compound 39732

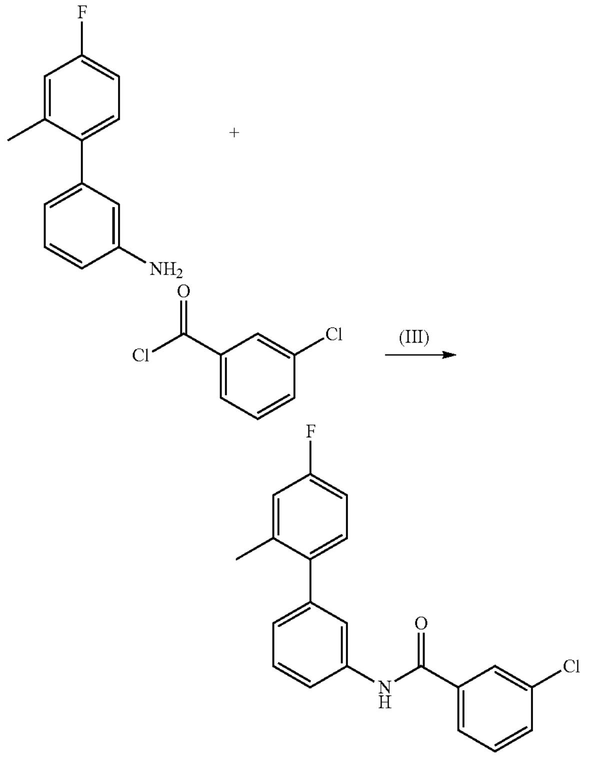

4'-fluoro-2'-methyl-[1,1'-biphenyl]-3-amine (1 eq) was added to a dry flask containing triethylamine (3 eq) dissolved in 5 ml of dichloromethane at room temperature. The flask was sealed and purged with Argon gas. 3-Chlorobenzoyl chloride (1.1 eq) was then added slowly to the reaction flask while stirring the mixture. The reaction was then allowed to proceed at room temperature for 24 h. After 24 h, the reaction mixture was evaporated under reduced pressure and the crude product was purified by column chromatography over silica gel eluting with 10% ethyl acetate in hexanes to give a white powder (KKL-39732) in quantitative yield. $^1$H-NMR ($CDCl_3$, 400 MHz): δ 2.26 (s, 3H), 6.86-7.00 (m, 2H), 7.08 (d, J=8.0 Hz, 1H), 7.13-7.20 (m, 1H), 7.35-7.44 (m, 2H), 7.50 (d, J=8.0 Hz, 1H), 7.54-7.64 (m, 2H), 7.73 (d, J=8.0 Hz, 1H), 7.84 (s, 1H), 7.98 (s, 1H). $^{13}$C-NMR ($CDCl_3$, 100 MHz): δ 20.7, 112.7, 116.8, 119.0, 121.4, 125.3, 126.0, 127.5, 129.0, 130.2, 131.2, 132.1, 135.1, 136.8, 137.4, 137.6, 137.9, 142.2, 161.0, 163.4, 164.6.

Synthesis of Compound 39733

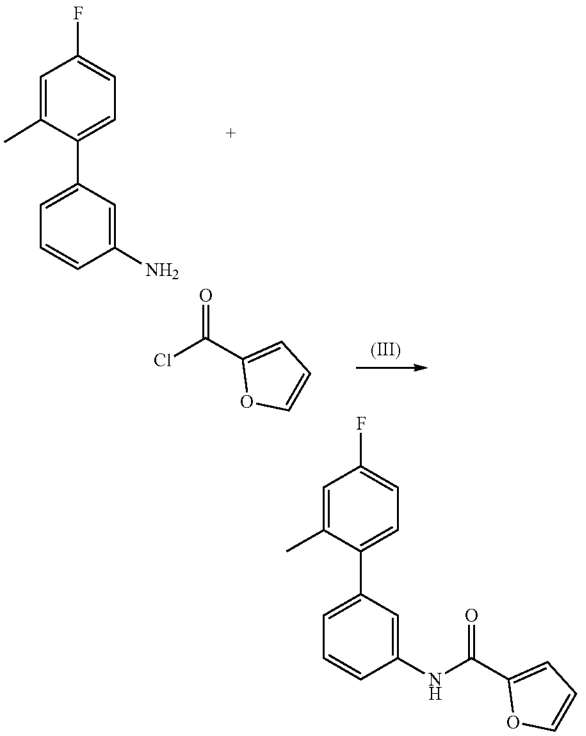

4'-fluoro-2'-methyl-[1,1'-biphenyl]-3-amine (1 eq) was added to a dry flask containing triethylamine (3 eq) dissolved in 5 ml of dichloromethane at room temperature. The flask was sealed and purged with Argon gas. 2-furoyl chloride (1.1 eq) was then added slowly to the reaction flask while stirring the mixture. The reaction was then allowed to proceed at room temperature for 24 h. After 24 h, the reaction mixture was evaporated under reduced pressure and the crude product was purified by column chromatography over silica gel eluting with 15% ethyl acetate in hexanes to give a white powder in quantitative yield. $^1$H-NMR ($CDCl_3$, 400 MHz): δ 2.33 (s, 3H), 6.55 (s, 1H), 6.82-6.99 (m, 2H), 7.26 (s, 1H), 7.32 (t, J=8.0 Hz, 1H), 7.57 (m, 2H), 7.89 (s, 1H), 7.73 (d, J=8.0 Hz, 1H), 7.84 (bs, 1H). $^{13}$C-NMR ($CDCl_3$, 100 MHz): δ 20.1, 112.7, 113.9, 115.5, 117.0, 118.6, 123.2, 124.7, 129.6, 129.8, 136.8, 138.0, 139.1, 139.6, 146.3, 148.7, 157.9, 161.9, 163.4.

Example 6—Bacterial Growth Inhibition by the Exemplified Compounds

Assay: Broth microdilution by the method of: Clinical and Laboratory Standards Institute, Ed., *Methods for dilution antimicrobial susceptibility tests for bacteria that grow aerobically: M07-A10; approved standard* (Committee for Clinical Laboratory Standards, Wayne, PA, 10. ed., 2015), *Documents/Clinical and Laboratory Standards Institute*. Results for bacterial growth inhibition by the exemplified compounds are shown in Table 3.

TABLE 3

| No. | MIC (μg/ml) | $IC_{50}$ (μg/ml) |
|---|---|---|
| 2170 | 14 | 6.8 |
| 39704 | 1.7-3.5 | 0.9-2.8 |
| 39705 | 34 | 16 |
| 39709 | 117 | n/d |
| 39710 | 51 | n/d |
| 39711 | 6.2 | 3.7 |
| 39712 | 21 | n/d |
| 39713 | 87 | n/d |
| 39714 | 64 | n/d |
| 39715 | 75 | n/d |
| 39717 | 50 | n/d |
| 39718 | 35 | n/d |
| 39720 | 4.3 | 2.4 |
| 39721 | 20 | n/d |
| 39722 | 73 | n/d |
| 39724 | 3.3-4.1 | 1.6-2.3 |
| 39730 | 66 | n/d |
| 39731 | 7.6 | 1.6-3.4 |
| 39732 | 8.5 | 5.9 |
| 39733 | 29 | 16 |
| 39734 | 28 | 22 |
| 39735 | 35 | n/d |
| 39739 | 38 | n/d |
| 39744 | 14 | n/d |
| 39748 | 7.6 | 2.6 |
| 39751 | 8.5 | 4.6 |

(n/d = not determined)

Example 7—Sigma E Inhibition Activity for Selected Compounds

The selected exemplified compounds were tested for inhibition of $\sigma^E$-mediated transcription using an *E. coli* reporter assay according to the protocol described in U.S. Pat. No. 8,962,550, which is incorporated herein by reference. As can be seen in Table 4, compounds caused dose-dependent inhibition of $\sigma^E$-mediated transcription, indicating target-based activity. For example, for compounds 39748 and 39751 the $IC_{50}$ for transcription inhibition was the same as the $IC_{50}$ for growth inhibition, demonstrating a correlation between target-based inhibition and antibiotic activity. Some tested compounds precipitated at high concentrations in the growth medium required for the transcription assay, hence the $IC_{50}$ determination for those compounds was affected by poor solubility in the growth medium.

TABLE 4

| No. | $IC_{50}$ |
|---|---|
| 39704 | 11* |
| 39720 | ~34.1* |
| 39724 | 6.6 |
| 39731 | ~60* |
| 39748 | 2.6 |
| 39751 | 4.3 |

*poor solubility in test medium.

Example 8—Toxicity of Selected Compounds

Assay: HUVEC (Human Umbilical Vein Endothelial Cells) and HeLa (cervical cancer cells) were seeded into 96-well culture plates at a density of $1.5\times10^5$ cells/ml in endothelial cell or DMEM growth medium, supplemented with 10% fetal bovine serum and no antibiotic. Cells were cultured for 24 h before assay setup. Compounds were diluted in the corresponding growth medium and tested in triplicate at 10× and 20× the minimum bacterial growth inhibitory concentrations. Growth media in the 96-well plate was aspirated off and replaced with media containing the test compounds or DMSO (0.5%, vol/vol). The plates were incubated at 37° C. in a 5% $CO_2$ incubator for 24 h. A positive control sample was prepared by replacing media in designated wells with a solution containing a cell lysis reagent. Propidium iodide was then added at 5 μM/well and the plate was incubated for 10 minutes at room temperature. Fluorescence was then recorded using a SpectraMax i3 (Molecular Devices) at $\lambda_{ex}$ 535 nm/$\lambda_{em}$ 617 nm. Cytotoxicity was determined by quantifying the fluorescence values for each compound relative to the positive control (100% cell lysis). For selected exemplified compounds, cytotoxicity against HeLa and HuVEC cells was measured at 10× and 20×MIC. As shown in Table 5, none of the tested compounds exhibited cytotoxicity above background levels.

TABLE 5

| | Cytotoxicity at 10× MIC | | Cytotoxicity at 20× MIC | |
|---|---|---|---|---|
| No. | HeLa | HuVEC | HeLa | HuVEC |
| 39704 | 11 | 15 | 11 | 21 |
| 39720 | 8 | 10 | 8 | 10 |
| 39724 | 11 | 16 | 14 | 19 |
| 39731 | 8 | 14 | 10 | 14 |
| 39748 | 14 | 15 | 14 | 21 |
| 39751 | 9 | 17 | 7 | 14 |
| DMSO control | 12 | 17 | 12 | 17 |

Example 9—Pharmacokinetic Data for Selected Compounds

Pharmacokinetic data for selected compounds is shown in Table 6. Stability in human liver microsomes ("HLM") showed slow degradation rates, with all tested compounds at least twice as stable as the midazolam control. For compound 39704, the $IC_{50}$ for CYP inhibition was more than 5× over the MIC, and no detectable inhibition of CYP was observed, for example, for compounds 39731 and 39751. All of the compounds exhibited substantial serum and plasma binding. Compounds 39704 and KKL-39751 had no detectable free compound, and the others were between 99.5 and 99.8% bound.

TABLE 6

| No. | $A^1$ | $B^2$ | $C^3$ | $D^4$ |
|---|---|---|---|---|
| 39704 | 5.38 | 13.5 | 99.9 | 100 |
| 39720 | 1.51 | N.D. | N.D. | N.D. |
| 39724 | 0.37 | 3.55 | 99.5 | 94.6 |
| 39731 | 2.12 | >33 | 99.8 | 99.7 |
| 39748 | 1.28 | 1.48 | 99.7 | 99.7 |
| 39751 | 4.35 | >33 | 99.9 | 99.9 |
| Midazolam control | 9.04 | | | |
| Positive control | | 0.02 | | |

[1]A Human Liver Microsomes Intrinsic Clearance ($CL_{int}$) (mL/min/g liver).
[2]B HLM CYP inhibition $IC_{50}$ (μM).
[3]C % plasma binding.
[4]D % serum binding.

Numbered Paragraphs

In some embodiments, the invention of the present disclosure can be described by reference to the following numbered paragraphs.

Paragraph 1. A compound of Formula (I):

(I)

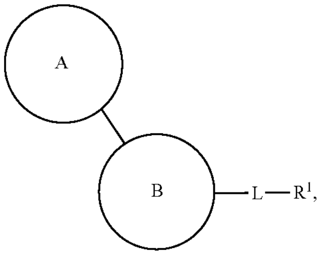

or a pharmaceutically acceptable salt thereof, wherein:

ring A is selected from $C_{6-10}$ aryl and $C_{3-10}$ cycloalkyl, each of which is optionally substituted with 1, 2, 3, 4, or 5 substituents independently selected from $R^A$;

ring B is selected from phenyl and pyridinyl, each of which is optionally substituted with 1, 2, 3, 4, or 5 substituents independently selected from $R^B$;

L is selected from $NR^2$, $C_{1-6}$ alkylene, —$N(R^2)C(=O)$—, —$C(=O)N(R^2)$—, —$N(R^2)S(=O)_2$—, —$S(=O)_2N(R^2)$—, S, O, C(=O), $S(=O)_2$, and 5-6-membered heteroaryl, wherein said 5-6-membered heteroaryl is optionally substituted with 1, 2, or 3 substituents independently selected from $R^3$;

$R^1$ is selected from $C_{6-10}$ aryl, 5-6-membered heteroaryl, and 4-7 membered heterocycloalkyl, each of which is optionally substituted with 1, 2, 3, 4, or 5 substituents independently selected from $R^3$;

each $R^2$ is independently selected from H, $C_{1-6}$ alkyl, $C_{1-6}$ haloalkyl, $C_{2-6}$ alkenyl, $C_{2-6}$ alkynyl, $Cy^1$, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^A$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^1$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^B$ is independently selected from halo, CN, $NO_2$, $C_{1-6}$ alkyl, $C_{1-6}$ haloalkyl, $C_{2-6}$ alkenyl, $C_{2-6}$ alkynyl, $Cy^1$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Cy^1$, $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $R^3$ is independently selected from halo, CN, $NO_2$, $C_{1-6}$ alkyl, $C_{1-6}$ haloalkyl, $C_{2-6}$ alkenyl, $C_{2-6}$ alkynyl, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Si(R^{b2})_3$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$;

each $Cy^1$ is independently selected from $C_{6-10}$ aryl, $C_{3-7}$ cycloalkyl, 5-10 membered heteroaryl, and 4-7 membered heterocycloalkyl, each of which is optionally substituted with 1, 2, 3, or 4 substituents independently selected from $R^g$;

each $R^{a1}$, $R^{b1}$, $R^{a2}$, and $R^{b2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$, $R^{d1}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 2. The compound of paragraph 1, wherein ring A is $C_{6-10}$ aryl, optionally substituted with 1 or 2 independently selected $R^A$.

Paragraph 3. The compound of paragraph 2, wherein ring A is phenyl, optionally substituted with 1 or 2 independently selected $R^A$.

Paragraph 4. The compound of paragraph 1, wherein ring A is $C_{3-10}$ cycloalkyl, optionally substituted with 1 or 2 independently selected $R^A$.

Paragraph 5. The compound of paragraph 4, wherein ring A is cyclohexyl, optionally substituted with 1 or 2 independently selected $R^A$.

Paragraph 6. The compound of any one of paragraphs 1-5, wherein ring B is phenyl, optionally substituted with 1 or 2 independently selected $R^B$.

Paragraph The compound of any one of paragraphs 1-5, wherein ring B is pyridinyl, optionally substituted with 1 or 2 independently selected $R^B$.

Paragraph 8. The compound of paragraph 1, wherein the compound of Formula (I) has formula:

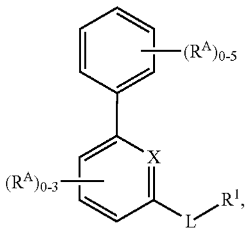

or a pharmaceutically acceptable salt thereof, wherein X is selected from N, CH, and $CR^B$.

Paragraph 9. The compound of paragraph 8, wherein the compound of Formula (I) has formula:

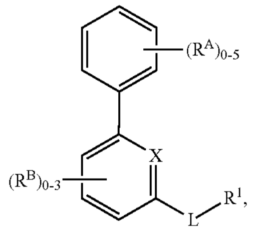

or a pharmaceutically acceptable salt thereof.

Paragraph 10. The compound of paragraph 9, wherein the compound of Formula (I) has formula:

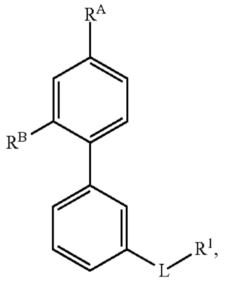

or a pharmaceutically acceptable salt thereof.

Paragraph 11. The compound of paragraph 8, wherein the compound of Formula (I) has formula:

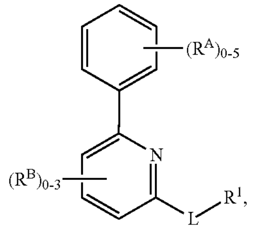

or a pharmaceutically acceptable salt thereof.

Paragraph 12. The compound of paragraph 11, wherein the compound of Formula (I) has formula:

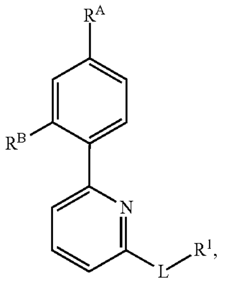

or a pharmaceutically acceptable salt thereof.

Paragraph 13. The compound of any one of paragraphs 1-12, wherein L is selected from $NR^2$, $C_{1-6}$ alkylene, —$N(R^2)C(=O)$—, —$N(R^2)S(=O)_2$—, and 5-6-membered heteroaryl, wherein said 5-6-membered heteroaryl is optionally substituted with 1 or 2 substituents independently selected from $R^3$.

Paragraph 14. The compound of paragraph 13, wherein L is $NR^2$.

Paragraph 15. The compound of paragraph 13, wherein L is —$N(R^2)C(=O)$—.

Paragraph 16. The compound of paragraph 13, wherein L is —$N(R^2)S(=O)_2$—.

Paragraph 17. The compound of any one of paragraphs 1-15, wherein $R^2$ is selected from H, $C_{1-6}$ alkyl, $C_{1-6}$ haloalkyl, $C_{2-6}$ alkenyl, and $C_{2-6}$ alkynyl.

Paragraph 18. The compound of paragraph 17, wherein $R^2$ is H.

Paragraph 19. The compound of paragraph 13, wherein L is $C_{1-6}$ alkylene.

Paragraph 20. The compound of paragraph 13, wherein the 5-6-membered heteroaryl is selected from oxadiazolyl, thiadiazolyl, thiophenyl, and triazolyl.

Paragraph 21. The compound of paragraph 13, wherein the 5-6-membered heteroaryl is triazlolyl of formula:

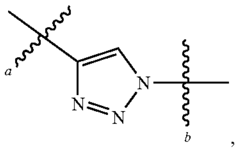 [SMILES: *c1cn(*)nn1], wherein a indicates a point of attachment to ring B and b indicates a point of attachment to $R^1$.

Paragraph 22. The compound of any one of paragraphs 1-21, wherein $R^1$ is $C_{6-10}$ aryl, optionally substituted with 1, 2, or 3 substituents independently selected from $R^3$.

Paragraph 23. The compound of paragraph 22, wherein $R^1$ is selected from phenyl and naphthyl, each of which is optionally substituted with 1 or 2 independently selected $R^3$.

Paragraph 24. The compound of any one of paragraphs 1-21, wherein $R^1$ is 5-6-membered heteroaryl, optionally substituted with 1 or 2 independently selected $R^3$.

Paragraph 25. The compound of paragraph 24, wherein $R^1$ is selected from pyridinyl, benzooxadiazolyl, quinolinyl, furyl, thiophenyl, imidazolyl, and oxadiazolyl, each of which is optionally substituted with 1 or 2 independently selected $R^3$.

Paragraph 26. The compound of any one of paragraphs 1-21, wherein $R^1$ is 4-7 membered heterocycloalkyl, optionally substituted with 1 or 2 independently selected $R^3$.

Paragraph 27. The compound of paragraph 26, wherein $R^1$ is selected from tetrahydropyran, tetrahydrothiopyran, morpholinyl, and piperidinyl, each of which is optionally substituted with 1 or 2 independently selected from $R^3$.

Paragraph 28. The compound of any one of paragraphs 1-27, wherein each $R^3$ is independently selected from halo, CN, $NO_2$, $C_{1-6}$ alkyl, $C_{1-6}$ haloalkyl, $C_{2-6}$ alkynyl, $N_3$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{2-6}$ alkynyl is optionally substituted with $Si(R^{b2})_3$.

Paragraph 29. The compound of paragraph 28, wherein each $R^3$ is independently selected from halo, $NO_2$, $C_{1-6}$ alkyl, $C_{1-6}$ haloalkyl, $C_{2-6}$ alkynyl, $N_3$, $NR^{c1}R^{d1}$, and $S(O)_2R^{b1}$; wherein said $C_{2-6}$ alkynyl is optionally substituted with $Si(R^{b2})_3$.

Paragraph 30. The compound of any one of paragraph 1-29, wherein each $R^4$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)$ $OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl is optionally substituted with a substituent selected from $Cy^1$, $OR^{a2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$.

Paragraph 31. The compound of paragraph 30, wherein each $R^A$ is independently selected from halo, $NO_2$, OH, $C_{1-6}$ alkyl, $C_{1-6}$ alkoxy, $C_{1-6}$ haloalkyl, and $C_{1-6}$ haloalkoxy.

Paragraph 32. The compound of paragraph 31, wherein each $R^A$ is independently selected from halo, $C_{1-6}$ alkyl, and $C_{1-6}$ haloalkyl.

Paragraph 33. The compound of any one of paragraphs 1-32, wherein each $R^B$ is independently selected from halo, $C_{1-6}$ alkyl, $C_{1-6}$ haloalkyl, and $OR^{a1}$; wherein each $C_{1-6}$ alkyl is optionally substituted with a substituent selected from $Cy^1$, $OR^{a2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$.

Paragraph 34. The compound of paragraph 33, wherein each $R^B$ is independently selected from halo, OH, $C_{1-6}$ alkyl, $C_{1-6}$ alkoxy, $C_{1-6}$ haloalkyl, and $C_{1-6}$ haloalkoxy.

Paragraph 35. The compound of paragraph 1, wherein:

L is selected from $NR^2$, $C_{1-6}$ alkylene, $—N(R^2)C(=O)—$, $—N(R^2)S(=O)_2—$, and 5-6-membered heteroaryl;

each $R^2$ is independently selected from H, $C_{1-6}$ alkyl, and $C_{1-6}$ haloalkyl;

$R^1$ is selected from $C_{6-10}$ aryl, 5-6-membered heteroaryl, and 4-7 membered heterocycloalkyl, each of which is optionally substituted with 1 or 2 substituents independently selected from $R^3$;

each $R^3$ is independently selected from halo, CN, $NO_2$, $C_{1-6}$ alkyl, $C_{1-6}$ haloalkyl, $C_{2-6}$ alkynyl, $N_3$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{2-6}$ alkynyl is optionally substituted with $Si(R^{b2})_3$;

each $R^A$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$, wherein said $C_{1-6}$ alkyl is optionally substituted with a substituent selected from $Cy^1$, $OR^{a2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; and each $R^B$ is independently selected from halo, $C_{1-6}$ alkyl, $C_{1-6}$ haloalkyl, and $OR^{a1}$; wherein each $C_{1-6}$ alkyl is optionally substituted with a substituent selected from $Cy^1$, $OR^{a2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$.

Paragraph 36. The compound of paragraph 1, wherein:

L is selected from NH, $—NHC(=O)—$, $—NHS(=O)_2—$, and triazolyl;

$R^1$ is selected from phenyl, naphthyl, pyridinyl, benzooxadiazolyl, quinolinyl, furyl, and tetrahydrothiopyranyl, each of which is optionally substituted with 1 or 2 substituents independently selected from $R^3$;

each $R^3$ is independently selected from halo, $NO_2$, $C_{1-6}$ alkyl, $C_{1-6}$ haloalkyl, $C_{2-6}$ alkynyl, $N_3$, $NR^{c1}R^{d1}$, and $S(O)_2R^{b1}$; wherein said $C_{2-6}$ alkynyl is optionally substituted with $Si(R^{b2})_3$;

each $R^A$ is independently selected from halo, $NO_2$, OH, $C_{1-6}$ alkyl, $C_{1-6}$ alkoxy, $C_{1-6}$ haloalkyl, and $C_{1-6}$ haloalkoxy; and each $R^B$ is independently selected from halo, OH, $C_{1-6}$ alkyl, $C_{1-6}$ alkoxy, $C_{1-6}$ haloalkyl, and $C_{1-6}$ haloalkoxy.

Paragraph 37. The compound of paragraph 1, wherein the compound is selected from any one of the compounds of Table 1, or a pharmaceutically acceptable salt thereof.

Paragraph 38. The compound of paragraph 1, wherein the compound is selected from any one of the compounds of Table 2, or a pharmaceutically acceptable salt thereof.

Paragraph 39. A pharmaceutical composition comprising a compound of any one of paragraphs 1-38, or a pharmaceutically acceptable salt thereof, and a pharmaceutically acceptable carrier.

Paragraph 40. A cleaning composition comprising a compound of any one of paragraphs 1-38, or a pharmaceutically acceptable salt thereof, and a carrier suitable for use in the cleaning composition.

Paragraph 41. A method of inhibiting conserved transcription factor σE of a bacteria, the method comprising contacting the bacteria with an effective amount of a compound of any one of paragraph 1-38, or a pharmaceutically acceptable salt thereof.

Paragraph 42. A method of inhibiting virulence of a bacteria, the method comprising contacting the bacteria with an effective amount of a compound of any one of paragraph 1-38, or a pharmaceutically acceptable salt thereof.

Paragraph 43. A method of killing bacteria or reducing growth of a bacteria, the method comprising contacting the bacteria with an effective amount of a compound of any one of paragraph 1-38, or a pharmaceutically acceptable salt thereof.

Paragraph 44. The method of any one of paragraphs 41-43, wherein the bacteria is contacted in vitro.

Paragraph 45. The method of any one of paragraphs 41-43, wherein the bacteria is contacted in vivo.

Paragraph 46. The method of any one of paragraphs 41-43, wherein the bacteria is contacted ex vivo.

Paragraph 47. The method of any one of paragraphs 41-46, wherein the bacteria is Gram-negative.

Paragraph 48. The method of paragraph 47, wherein the bacteria is a member of a genus selected from: *Acinetobacter, Burkholderia, Acinetobacter, Burkholderia, Klebsiella, Pseudomonas*, and *Escherichia.*

Paragraph 49. The method of paragraph 47, wherein the bacteria is selected from *E. coli, K. pneumoniae, P aeruginosa*, and *A. baumannii.*

Paragraph 50. The method of any one of paragraphs 41-46, wherein the bacteria is Gram-positive.

Paragraph 51. The method of paragraph 50, wherein the bacteria is a member of a genus selected from: *Staphylococcus, Streptococcus, Propionibacterium, Peptococcus, Enterococcus*, and *Bacillus.*

Paragraph 52. The method of paragraph 50, wherein the Gram-positive bacteria is selected from: *S. aureus, S. pyogenes, S. pneumoniae, S. salivarius, S. milleri, S. mutans, P acnes, E. faecalis, E. faecium, B. subtilis*, and *B. anthracis.*

Paragraph 53. A method of cleaning or sanitizing a surface, the method comprising contacting the surface with an effective amount of a compound of any one of paragraph 1-38, or a pharmaceutically acceptable salt thereof.

Paragraph 54. A method of treating a bacterial infection, the method comprising administering to a subject in need thereof a therapeutically effective amount of a compound of any one of paragraphs 1-38, or a pharmaceutically acceptable salt thereof.

Paragraph 55. The method of paragraph 54, wherein the bacterial infection is selected from: skin infection, connective tissue infection, bone infection, joint or muscle infection, wound infection, endovascular infection, CNS infection, abdominal infection, blood stream infection, urinary tract infection, pelvic infection, invasive systemic infection, gastrointestinal infection, abdominal infection or abscess, abscess of any short, intrathoracic infection, and dental infection.

Paragraph 56. The method of paragraph 54, wherein the bacterial infection is selected from: skin acne, septic arthritis, atopic dermatitis, sinusitis, food poisoning, abscess, pneumonia, meningitis, osteomyelitis, endocarditis, bacteremia, sepsis, and urinary tract infection.

Paragraph 57. The method of any one of paragraphs 54-56, comprising administering to the subject a therapeutically effective amount of at least one additional therapeutic agent, or a pharmaceutically acceptable salt thereof.

Paragraph 58. The method of paragraph 57, wherein the additional therapeutic agent is an antibiotic, or a pharmaceutically acceptable salt thereof.

Paragraph 59. The method of paragraph 58, wherein the antibiotic is selected from a β-lactam and a cephalosporin, or a pharmaceutically acceptable salt thereof.

Paragraph 60. The method of any one of paragraphs 57-59, wherein the compound of any one of paragraphs 1-38, or a pharmaceutically acceptable salt thereof, and the additional therapeutic agent, or a pharmaceutically acceptable salt thereof, are administered to the subject consecutively or simultaneously.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (I):

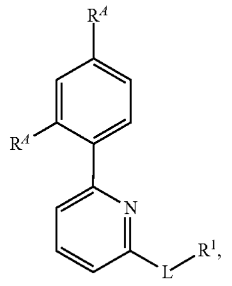

or a pharmaceutically acceptable salt thereof, wherein:

L is selected from NH, —NHC(═O)—, and triazolyl;

$R^1$ is selected from phenyl, naphthyl, pyridinyl, benzooxadiazolyl, quinolinyl, furyl, and tetrahydrothiopyranyl, each of which is optionally substituted with 1 or 2 substituents independently selected from $R^3$;

each $R^A$ is independently selected from halo, $NO_2$, OH, $C_{1-6}$ alkyl, $C_{1-6}$ alkoxy, $C_{1-6}$ haloalkyl, and $C_{1-6}$ haloalkoxy;

each $R^3$ is independently selected from halo, $NO_2$, $C_{1-6}$ alkyl, $C_{1-6}$ haloalkyl, $C_{2-6}$ alkynyl, $N_3$, $NR^{c1}R^{d1}$, and $S(O)_2R^{b1}$, wherein said $C_{2-6}$ alkynyl is optionally substituted with $Si(R^{b2})_3$;

each $R^{b1}$ and $R^{b2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are optionally substituted with 1, 2, 3, 4, or 5 substituents independently selected from $R^g$;

each $R^{c1}$ and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene is optionally substituted with 1, 2, 3, 4, or 5 substituents independently selected from $R^g$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. A compound selected from any one of the following compounds:

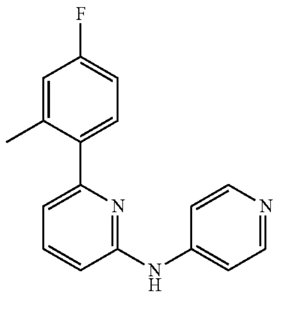

-continued
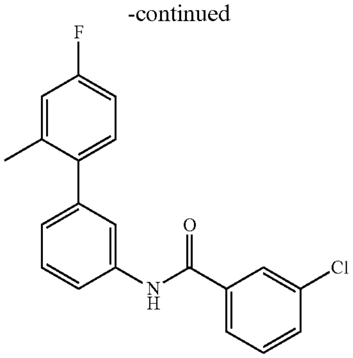
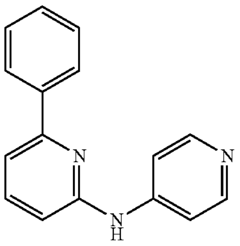
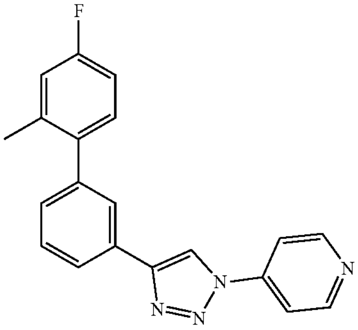
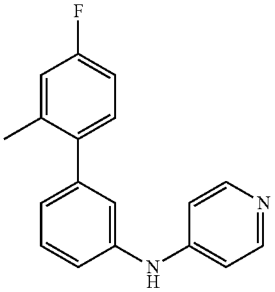
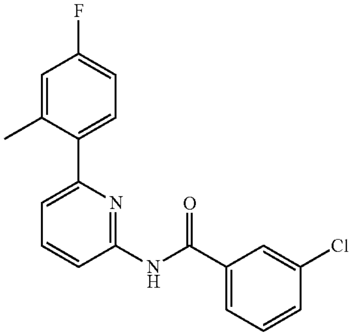
-continued
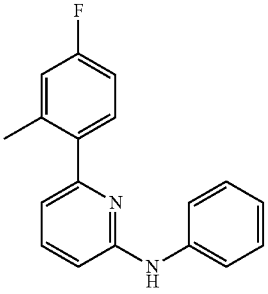
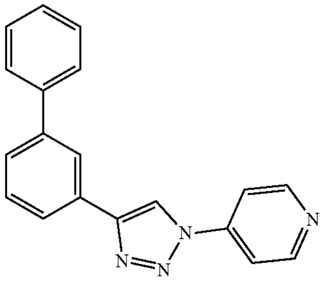
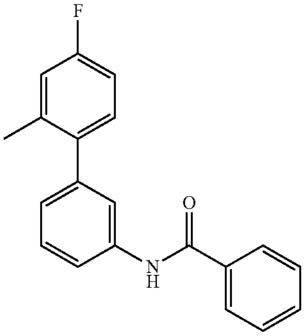
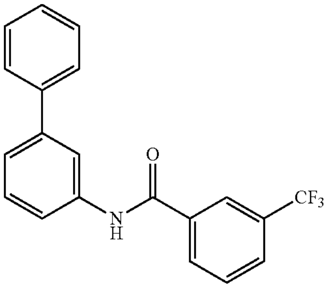
or a pharmaceutically acceptable salt thereof.
3. A compound selected from any one of the following compounds:
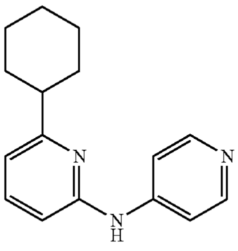
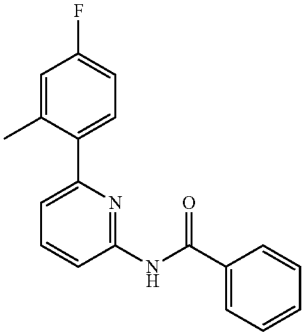

-continued
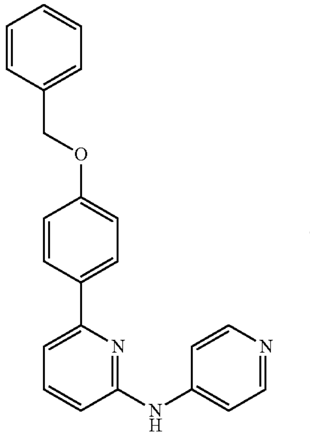
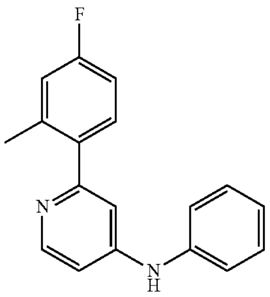
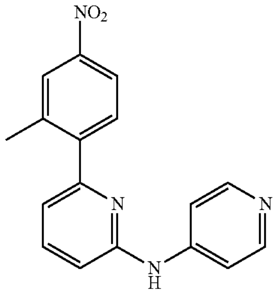
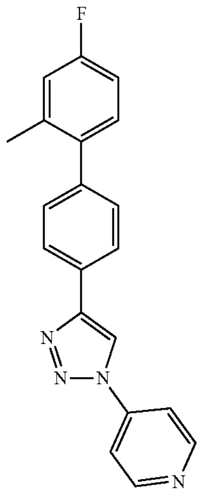
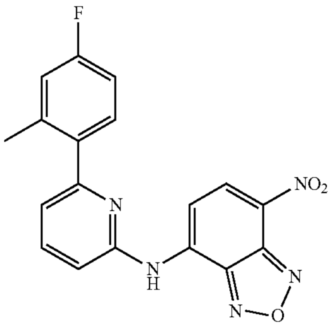
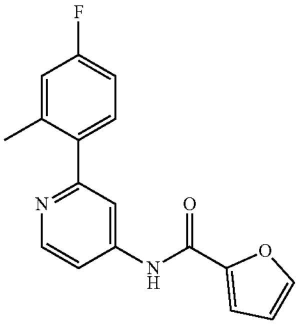
-continued
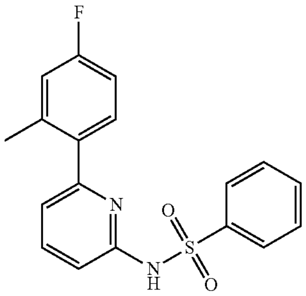
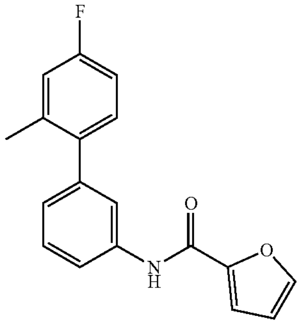
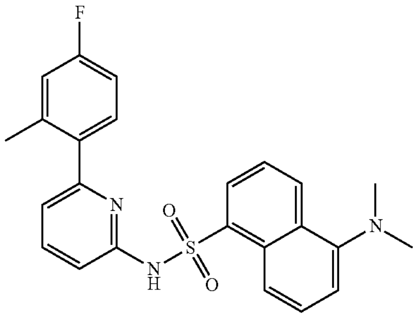
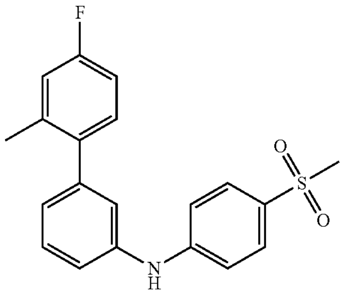
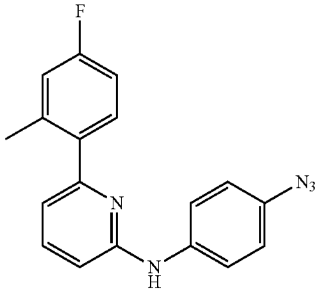

-continued

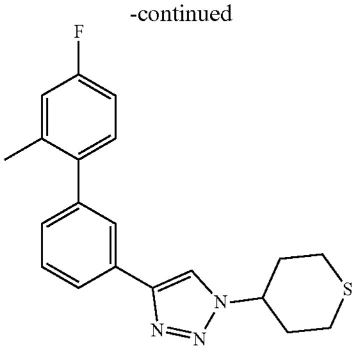

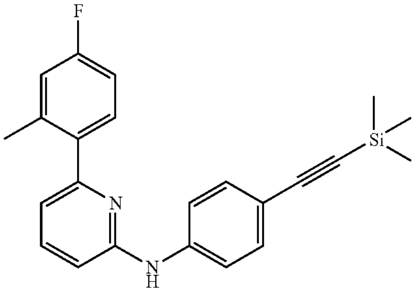

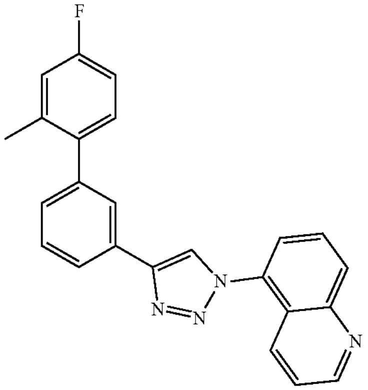

or a pharmaceutically acceptable salt thereof.

4. A pharmaceutical composition comprising a compound of claim 1, or a pharmaceutically acceptable salt thereof, and a pharmaceutically acceptable carrier.

5. A cleaning composition comprising a compound of claim 1, or a pharmaceutically acceptable salt thereof, and a carrier suitable for use in the cleaning composition.

6. A method of cleaning or sanitizing a surface, the method comprising contacting the surface with an effective amount of a compound of claim 1, or a pharmaceutically acceptable salt thereof.

7. A method of treating a bacterial infection, the method comprising administering to a subject in need thereof a therapeutically effective amount of a compound of claim 1, or a pharmaceutically acceptable salt thereof.

8. The method of claim 7, wherein the bacterial infection is selected from: skin infection, connective tissue infection, bone infection, joint or muscle infection, wound infection, endovascular infection, CNS infection, abdominal infection, blood stream infection, urinary tract infection, pelvic infection, invasive systemic infection, gastrointestinal infection, abdominal infection or abscess, abscess of any short, intrathoracic infection, and dental infection.

9. The method of claim 7, comprising administering to the subject a therapeutically effective amount of at least one additional antibiotic selected from a β-lactam and a cephalosporin, or a pharmaceutically acceptable salt thereof.

10. A pharmaceutical composition comprising a compound of claim 2, or a pharmaceutically acceptable salt thereof, and a pharmaceutically acceptable carrier.

11. A cleaning composition comprising a compound of claim 2, or a pharmaceutically acceptable salt thereof, and a carrier suitable for use in the cleaning composition.

12. A method of cleaning or sanitizing a surface, the method comprising contacting the surface with an effective amount of a compound of claim 2, or a pharmaceutically acceptable salt thereof.

13. A method of treating a bacterial infection, the method comprising administering to a subject in need thereof a therapeutically effective amount of claim 2, or a pharmaceutically acceptable salt thereof.

14. The method of claim 13, wherein the bacterial infection is selected from: skin infection, connective tissue infection, bone infection, joint or muscle infection, wound infection, endovascular infection, CNS infection, abdominal infection, blood stream infection, urinary tract infection, pelvic infection, invasive systemic infection, gastrointestinal infection, abdominal infection or abscess, abscess of any short, intrathoracic infection, and dental infection.

15. A pharmaceutical composition comprising a compound of claim 3, or a pharmaceutically acceptable salt thereof, and a pharmaceutically acceptable carrier.

16. A cleaning composition comprising a compound of claim 3, or a pharmaceutically acceptable salt thereof, and a carrier suitable for use in the cleaning composition.

17. A method of cleaning or sanitizing a surface, the method comprising contacting the surface with an effective amount of a compound of claim 3, or a pharmaceutically acceptable salt thereof.

18. A method of treating a bacterial infection, the method comprising administering to a subject in need thereof a therapeutically effective amount of claim 3, or a pharmaceutically acceptable salt thereof.

19. The method of claim 18, wherein the bacterial infection is selected from: skin infection, connective tissue infection, bone infection, joint or muscle infection, wound infection, endovascular infection, CNS infection, abdominal infection, blood stream infection, urinary tract infection, pelvic infection, invasive systemic infection, gastrointestinal infection, abdominal infection or abscess, abscess of any short, intrathoracic infection, and dental infection.

20. The compound of claim 1, wherein:

L is NH;

$R^1$ is selected from phenyl and pyridinyl, each of which is optionally substituted with 1 or 2 substituents independently selected from $R^3$;

each $R^3$ is independently selected from halo, $C_{2-6}$ alkynyl, $N_3$ and $S(O)_2R^{b1}$, wherein said $C_{2-6}$ alkynyl is optionally substituted with $Si(R^{b2})_3$; and each $R^A$ is independently selected from halo, $NO_2$, and $C_{1-6}$ alkyl.

* * * * *